United States Patent
Baraldi (12)

(10) Patent No.: US 6,323,214 B1
(45) Date of Patent: Nov. 27, 2001

(54) ALLOSTERIC ADENOSINE RECEPTOR MODULATORS

(75) Inventor: Pier Giovanni Baraldi, Ferrats (IT)

(73) Assignee: Medco Research, Inc, Bristol, TN (US)

( * ) Notice: Subject to any disclaimer, the term of this patent is extended or adjusted under 35 U.S.C. 154(b) by 0 days.

(21) Appl. No.: 09/156,077

(22) Filed: Sep. 17, 1998

Related U.S. Application Data

(63) Continuation-in-part of application No. 08/959,758, filed on Oct. 29, 1997.

(51) Int. Cl.[7] .................. S01N 43/42; A16K 31/385; C07D 471/025; C07D 197/00; C07D 333/38
(52) U.S. Cl. .................. 514/301; 514/430; 514/443; 546/114; 549/32; 549/71; 549/72; 549/73
(58) Field of Search .................. 546/114; 549/32, 549/71, 72, 73; 514/301, 439, 443

(56) References Cited

U.S. PATENT DOCUMENTS

| | | | |
|---|---|---|---|
| 3,558,606 | 1/1971 | Tinney | 260/239.3 |
| 5,026,698 | * 6/1991 | Fujikawa et al. | 514/215 |
| 5,532,233 | 7/1996 | Weber | 514/219 |
| 5,585,385 | 12/1996 | Natsugari et al. | 514/300 |
| 5,593,988 | 1/1997 | Tahara | 514/219 |
| 5,747,486 | 5/1998 | Sohda | 514/211 |

FOREIGN PATENT DOCUMENTS

| | | |
|---|---|---|
| 2233457 | 2/1973 | (DE) . |
| 2323149 | 11/1973 | (DE) . |
| 3724031 | 1/1988 | (DE) . |
| 407955 | 1/1991 | (EP) . |
| 393101 | 5/1974 | (ES) . |
| 5345785 | 12/1993 | (JP) . |
| 50011397 | 4/1995 | (JP) . |
| 7304755 | 11/1995 | (JP) . |
| 8337583 | 12/1996 | (JP) . |
| 93/07129 | 4/1993 | (WO) . |
| 96/14319 | 5/1996 | (WO) . |

OTHER PUBLICATIONS

CAS/Routh et al., "Techykinin Receptors in the Spinal Cord", *Progress in Brain Research*, 104: 93–108, 1995.

CAS/Chesselet et al., "Ischemic Damage in the Striatum of Adult Gerbils: Relative Sparing of Somatostatinergic . . . ", *Experimental Neurology*, 110(2) 209–218, 1990.

CAS/Cragg, et al., "Tachykinin Antagonists in carotid Body Responsews to Hypoxia and Substance P in the Rat", *Respiration Physiology*, 95(3): 295–310, 1994.

CAS/Benedek, et al., "Potentiation of Thermoregulatory and Analgesic Effects of Morphine by Calcium Antagonists", *Pharm. Res. Comm.*, 16(10): 1009–1018, 1994.

CAS/Ghio, et al., "Clinical Evaluation of Calcium–Antagonist Dgs", *J. Card. Pharm.*, 20:S71–74 1992.

CAS/Zhou, et al., "Effects of Calcium Blockers on the Performance of Left and Right Ventricles During Acute Hypoxia", *Sheng Lie Hseuh Poa*, 44(3): 237–243, 1992.

CAS/Ueno, et al., "Simultaneous Determiniation of a New Dihydropyridine Calcium Blocker and Its Pyridine Metabolite in Dog Plasma . . .", *Anal. Sci.*, 7(5): 727–731, 1991.

(List continued on next page.)

Primary Examiner—Mukund J. Shah
Assistant Examiner—TamThom N. Truong
(74) Attorney, Agent, or Firm—Roberts Abokhair & Mardula, LLC

(57) ABSTRACT

The present invention relates to compounds of formulas (IA), (IB), and (IC):

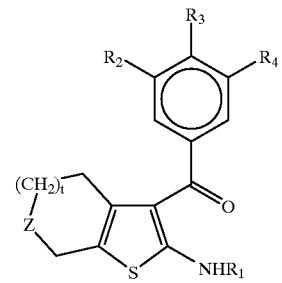

(IA)

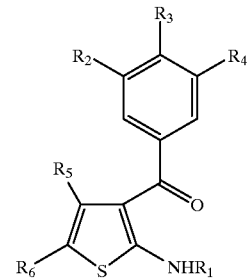

(IB)

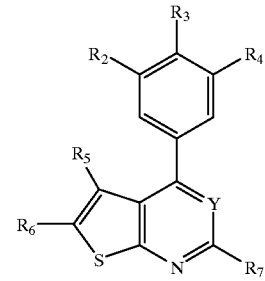

(IC)

the preparation thereof, pharmaceutical formulations thereof, and their use in medicine as allosteric adenosine receptor modulators for uses including protection against hypoxia and ischemia induced injury and treatment of adenosine-sensitive cardiac arrhythmias.

9 Claims, 16 Drawing Sheets

OTHER PUBLICATIONS

Leung et. al., "Enhancement of Adenosine A, Receptor . . . ", CA, vol. 123, 1995, p. 90, ABS# 123: 246602 W.*

Amoah–Apraku, B. et al., "Selective Potentiation by an $A_1$ Adenosine Receptor Enhancer of the Negative Dromotropic Action of Adenosine in the Guinea Pig Heart," The Journal of Pharmacology and Experimental Therapeutics, vol. 266, No. 2, pp. 611–617 (1993).

Bhattacharya, Samita et al., "Effects of Long–Term Treatment with the Allosteric Enhancer, PD81, 723, n Chinese Hamster Ovary Cells Expressing Recombinant Human $A_1$ Adenosine Receptors," Molecular Pharmacology, vol. 50, pp. 104–111 (1996).

Bhattacharya, Samita et al., "The Allosteric Enhancer, PD 81,723, Stabilizes Human $A_1$ Adenosine Receptor Coupling to G Proteins," Biochimica et Biophysica Acta, 1265: pp. 15–21, 1995.

Bruns, Robert et al., "Allosteric Enhancement of Adenosine $A_1$ Receptor Binding and Function by 2–Amino–3–benzoylthiophenes," Molecular Pharmacology, vol. 38, No. 6, pp. 939–949 (1990).

Bruns, Robert et al., "Structure–Activity Relationships for Enhancement of Adenosine $A_1$ Receptor Binding by 2–Amino–3benzoylthiophenes," Molecular Pharamacology, vol. 38, pp. 950–958 (1990).

Cao, X et al., "Adenosine $A_1$ Receptor Enhancer, PD 81,723, and Cerebral Ischemia/Refperfusion Injusry in the Gerbil," General Pharmacology, vol. 26, No. 7, pp. 1545–1548 (1995).

Corral, Carlos et al., "Reacciones de Bischler y de Friedlander con 2–amono–3–aroil–tiofenos", Afinidad, Mar.–Apr. (1978).

Dennis, Don M. et al., "Modulation of Atrioventricular Nodal Function by Metabolic and Allosteric Regulators Endogenous Adenosine in Guinea Pig Heart," Circulation, vol. 94, No. 10, pp. 2551–2559 (1996).

Fortea, Joan, "Thieno[2,3–d]pyrimidine 3–oxides. Synthesis and N–Oxide Reactions of 4–Phenyl–and 4–Aminothieno [2,3–d]pyrimidine 3–oxides," Journal Für praktische Chemie, Band 317, Heft 5, pp. 705–711 (1975).

Hromatka, O. et al., "Über die Nitrierung von 7–Chlor–5–phenyl–1 H–thieno[2,3–e]1, 4–diazepin–2(3H)–on," Monatshefte für Chemie, vol. 104, pp. 709–714 (1973).

Janusz, Cynthia A. et al., "Functional activity of the adenosine binding enhancer, PD 81,723, in the in vitro hippocampal slice", Brain Research, vol. 567, pp. 181–187 (1991).

Kollias–Baker, C. et al., "Novel Approach for Enhancing Atrioventricular Nodal Conduction Delay Mediated by Endogenous Adenosine," Circulation Research, vol. 75, No. 6, pp. 972–980 (1994).

Kollias–Baker, C. et al., "Allosteric Enhancer PD 81,723 Acts by Novel Mechanism to Potentiate Cardiac Actions of Adenosine," Circulation Research, vol. 75, No. 6, 961–971 (1994).

Kollias–Baker, Cynthia, "The Allosteric Enhancer, PD 81,723, Potentiates the Cardiac Effects of Adenosine by Enhancing the Binding of Agonists to $A_1$ Adenosine Receptors," A Dissertation presented to the Graduate School of the University of Florida (1994).

Leung, E. et al., "Enhancement of Adenosine $A_1$ Receptor Functions by Benzoylthiophenes in Guinea Pig Tissues in Vitro," Archives of Pharmacology, vol. 352, No. 2, pp. 206–212, (1995).

Mizumura, Tsuneo et al., "PD 81, 723, an Allosteric Enhancer of the $A_1$ Adenosine Receptor, Lowers the Threshold for Ischemic Preconditioning in Dogs ," Circulation Research, vol. 79, No. 3, pp. 415–423 (Sep. 1996).

Mudumbi, Ramagopal V. et al., "Cardia Functional Responses to Adensoine by PD 81, 723, an Allosteric Enhancer of the Adenosine $A_1$ Receptor," American Journal of Physiology, vol. 264, pp. H1071–H1022, 1992.

Nakanish, Michio et al., "Studies on Pcychotropic Drugs. 18.[1]Synthesis and Structure–Activity Relationships of 5–Phenyl–1,3–dihydro–2H–thieno[2,3–e][1,4] Diazepin–2–ones," Journal of Medicinal Chemistry, vol. 16, No 3. pp. 24–219 (1973).

Robba, Max et al., "No. 144—Thienopyrimidines. IX—Etude de la thieno[2,3–d] pyrimidines et de ses derives," Bulletin de la Societe Chimique de France, pp. 761–764 (1976).

* cited by examiner

ALLOSTERIC ADENOSINE RECEPTOR MODULATORS

This application is a continuation-in-part of U.S. Ser. No. 08/959,758, filed on Oct. 29, 1997 by Pier G. Baraldi, entitled "Allosteric Adenosine Receptor Modulators."

BACKGROUND OF THE INVENTION

FIELD OF THE INVENTION

The present invention relates to certain thiophene derivatives and their use in the practice of medicine as allosteric modulators of adenosine receptors.

Adenosine (Ado) is an autocoid (or local hormone) that modulates numerous functions in the cardiovascular and other organ systems. The actions of Ado are mediated by at least four subtypes of cell surface receptors called $A_1$, $A_{2a}$, $A_{2b}$, and $A_3$. Because of the ubiquity of adenosine receptors (AdoRs) throughout the human body, their indiscriminate activation may cause undesirable side effects. Therefore, it is desirable that drugs which are administered systemically to target these receptors have some degree of organ selectivity.

The overall function of Ado appears to be the regulation of the balance between oxygen (or energy) supply and consumption (or work). Ado increases oxygen supply by causing vasodilation and decreases oxygen consumption or work by inhibiting cellular functions, e.g., slowing of heart rate. Consistent with this protective function, $A_1$AdoR agonists, Ado uptake blockers and Ado deaminase inhibitors have been shown to reduce cellular damage and dysfunction during hypoxia and ischemia. This protective role of Ado and $A_1$AdoR agonists has been shown in heart, brain, liver, and intestines. This and other potentially beneficial actions of Ado have led to increased interest in the development of Ado-related drugs targeted to ameliorate conditions such as myocardial ischemia and stroke.

However, the widespread expression of Ado receptors and the lack of sufficiently selective adenosine agonists have been a major impediment to the successful development of direct-acting AdoR agonists to exploit the cytoprotective properties of Ado.

A number of compounds known to modulate the action of neurotransmitters, hormones and peptides bind at sites distinct from, but functionally linked to, the primary recognition site of the respective receptors. This form of interaction between two different ligands at the same receptor protein, which may result in modulation in the form of enhancement or inhibition of each other's binding and function, is referred to as allosterism. Positive (enhancement) or negative (inhibition) allosterism are important mechanisms of action of various biologically active agents. Numerous allosteric interactions have been exploited. Among the most well known of these are the allosteric interactions between the GABA receptor and benzodiazepines; the atrial natriuretic factor (ANF) receptor and amiloride; the dextromethorphan binding site and ropizine; and the muscarinic receptor and gallamine. Allosteric modulation of the actions of Ado on the $A$,AdoR by several 2-amino-3-benzoylthiophenes on cultured cells, cardiac and brain preparations have been reported. The specificity of these compounds for $A_1$AdoRs have also been demonstrated.

It would be advantageous to provide allosteric modulators of Ado as an alternative to direct-acting Ado agonists and nucleoside uptake blockers, preferably those which can selectively modulate the response to Ado in only those organs or localized areas of a given organ in which production of Ado is increased.

It is therefore an object of the present invention to provide allosteric modulators of Ado function.

It is a further object of the present invention to provide allosteric modulators of Ado function which provide a more selective therapeutic effect than direct-acting AdoR agonists.

It is still a further object of the present invention to provide methods of administering allosteric modulators of Ado function which limit the times and locations at which significant release of Ado occurs so that systemic side effects are minimized.

SUMMARY OF THE INVENTION

Compounds useful as potent, yet selective allosteric modulators of adenosine receptors, with activity as AdoR agonists, and, in some cases, AdoR antagonists, and methods of preparation and use thereof, are disclosed.

The compound have the following general formulas IA, IB, and IC:

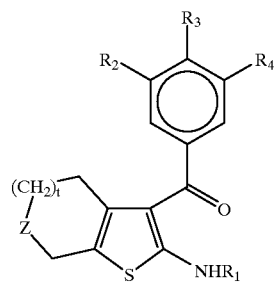

(IA)

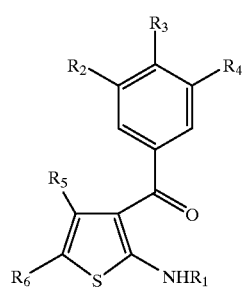

(IB)

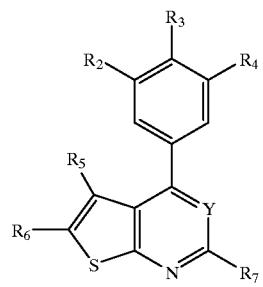

(IC)

wherein:
 $R_1$ is hydrogen, alkyl, substituted alkyl, or haloacetyl;
 $R_2$, $R_3$, and $R_4$ are independently hydrogen, halogen, alkyl, substituted alkyl, aryl, heteroaryl, heterocyclic, lower alkenyl, lower alkanoyl, amino, trifluoromethyl, amino alkyl, nitro, or cyano;
 t is 0, 1, 2, or 3;
 Z is NH, N—C(X)—NH-aryl, NC(X)—NH-alk, N—C(X)—O-alk, N—C(X)—O-alkaryl, N—C(X)—O— aryl, N(alk)$_2$ (+) (and an associated pharmaceutically acceptable anion such as F−, Cl−, Br− or I−), N—(Gr)$_m$(Am)$_n$(Alk)$_p$(Ar)$_q$, or CH—(Gr)$_m$(Am)$_n$(Alk)$_p$(Ar)$_q$, wherein Gr is —SO$_2$—, —C(O)O—, or —C(O)—, Am is —CH(NH$_2$)—, an amino acid residue, or an amino protected amino acid residue, Alk is hydrogen, alkylene, substituted alkylene, alkenylene or substituted alkenylene, Ar is aryl or substituted aryl, wherein the substituents include one or more alkyl or substituted alkyl groups or one or more nitro groups, m is 0 or 1 n, p, and q are independently 0, 1, or 2,
provided that at least one of m, n, p, and q is other than 0;

X is O, S or N-alk

R$_5$ and R$_6$ are independently hydrogen, alkyl, substituted alkyl, or taken together form a lower alkenyl ring of 5 or 6 members,
provided that if R$_2$, R$_3$, and R$_4$ are hydrogen, then both R$_5$ and R$_6$ may be neither hydrogen nor methyl;
further provided that if R$_2$ and R$_3$ are hydrogen while R$_4$ is trifluoromethyl or if R$_2$ and R$_4$ are hydrogen while R$_3$ is chloro, then both R$_5$ and R$_6$ may not be methyl;

R$_7$ is hydrogen, alkyl, N(alk)$_2$, substituted alkyl or OH (and the resulting tautomeric form in which the OH is tautomerized to a carbonyl and the imine is tautomerized to an NH group);

Y is nitrogen, CH, C—CN or C—C(O)OR$_8$; and
wherein R$_8$ is hydrogen, alkyl or substituted alkyl.

The compounds can be used in a method for allosterically modulating adenosine receptors in a mammal, including a human. The methods involve administering an effective amount of a compound of formula IA, IB, or IC sufficient to moderate adenosine receptors to the mammal. Positive allosterism results in several beneficial effects, including cardioprotection, neuroprotection, analgesia, and treatment of sleep disorders, irritable bowel syndrome, irritable bladder, urge incontinence, and glaucoma. Negative allosterism results in several beneficial effects, including the ability to treat Alzheimer's disease and congestive heart failure.

The compounds can be used in a pharmaceutical formulation that includes a compound of formula IA, IB, or IC and one or more excipients. Various chemical intermediates can be used to prepare the compounds of formula IA, IB, or IC.

BRIEF DESCRIPTION OF THE FIGURES

In FIG. 2A, the circles represent results from Compound/Example 21, and the squares represent results from Compound/Example 22. In FIG. 2B, the circles represent results from Compound/Example 20, and the squares represent results from Compound/Example 28. In FIG. 2C, the circles represent results from Compound/Example 7, and the squares represent results from Compound/Example 9. In FIG. 2D, the circles represent results from Compound/Example 10.

In FIG. 3A, the circles represent results from Compound/Example 13, and the squares represent results from Compound/Example 18. In FIG. 3B, the circles represent results from Compound/Example 24, and the squares represent results from Compound/Example 5. In FIG. 3C, the circles represent results from Compound/Example 27, and the squares represent results from Compound/Example 11. In FIG. 3D, the circles represent results from Compound/Example 16 and the squares represent results from Compound/Example 14.

DETAILED DESCRIPTION OF THE INVENTION

Figure 1A:
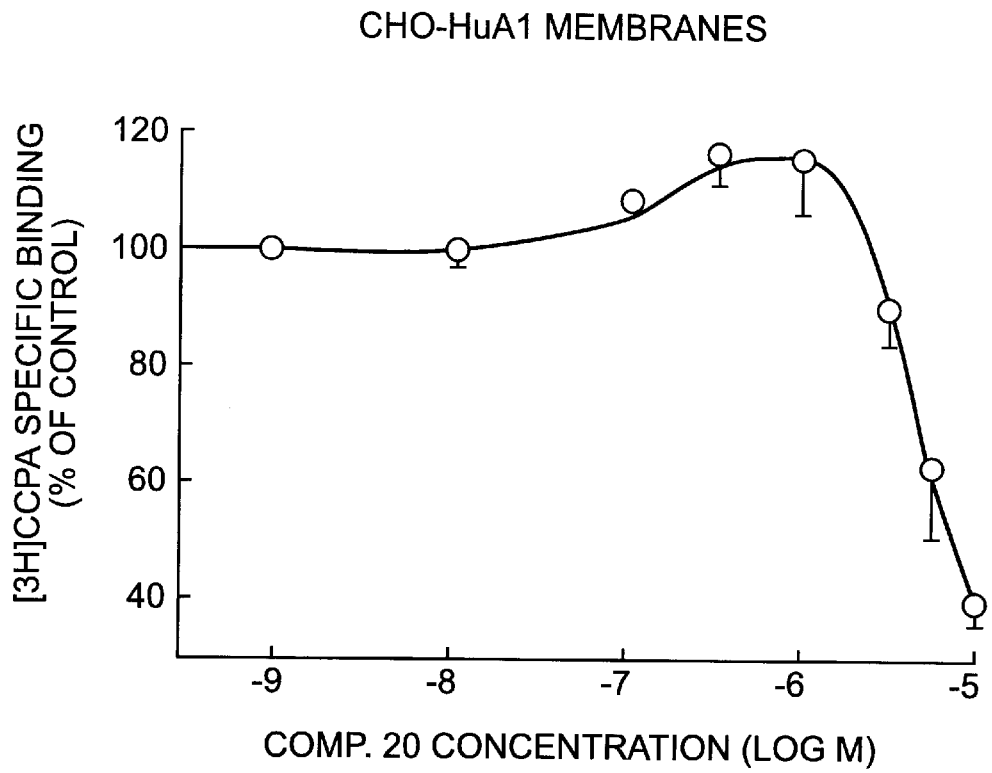
FIGS. 1A and 1B are graphs showing the specific binding (percent of control) of the agonist [$^3$H]2-chloro-N$^6$-cyclopentyladenosine ([$^3$H]CCPA) (FIG. 1A) and the antagonist [$^3$H]8-cyclopentyl-1,3-dipropylxanthine ([$^3$H]CPX) (FIG. 1B) as a function of concentration (log M) of the allosteric enhancer 2-amino-3-benzoyl-6-(3-methylbut-2-en-yl)-4,5,6,7-tetrahydrothieno[2,3-c]pyridine (Compound/Example number 20) to membranes from Chinese hamster ovary ("CHO") cells expressing recombinant human adenosine A1 receptor ("huA$_1$AdoR").

The present application discloses compounds useful as potent, yet selective allosteric modulators of adenosine receptors, with activity as AdoR agonists, and in some cases, AdoR antagonists, and methods of preparation and use thereof.

The compounds can be used in a method for allosterically modulating adenosine receptors in a mammal, including a human. The methods involve administering an effective amount of a compound of formula IA, IB, or IC sufficient to moderate adenosine receptors to the mammal.

The compounds can be used in a pharmaceutical formulation that includes a compound of formula IA, IB, or IC and one or more excipients. Various chemical intermediates can be used to prepare the compounds of formula IA, IB, or IC.

Definitions

As used herein, a compound is an agonist of an adenosine $A_1$ receptor if it is able to fully inhibit adenylate cyclase ($A_1$) and is able to displace [$^{125}$I]-AB-MECA in a competitive binding assay.

As used herein, a compound is a partial agonist of an adenosine $A_1$ receptor if it is able to partially inhibit adenylate cyclase ($A_1$) and is able to displace [$^{125}$I]-AB-MECA in a competitive binding assay.

As used herein, a compound is an antagonist of an adenosine $A_1$ receptor if it is able to prevent the inhibition due to an agonist and is able to displace [$^{125}$I]-AB-MECA in a competitive binding assay.

As used herein, the term "alkyl" refers to monovalent straight, branched or cyclic alkyl groups preferably having from 1 to 20 carbon atoms, more preferably 1 to 10 carbon atoms ("lower alkyl") and most preferably 1 to 6 carbon atoms. This term is exemplified by groups such as methyl, ethyl, n-propyl, iso-propyl, n-butyl, iso-butyl, n-hexyl, and the like. The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, the term "substituted alkyl" refers to an alkyl group, preferably of from 1 to 10 carbon atoms ("substituted lower alkyl"), having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino aminoacyl, aminoacyloxy, oxyacylamino, cyano, halogen, hydroxyl, keto, thioketo, carboxyl, carboxylalkyl, thiol, thioalkoxy, substituted thioalkoxy, aryl, aryloxy, heteroaryl, heteroaryloxy, heterocyclic, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from the group consisting of alkyl, aryl, heteroaryl and heterocyclic. As used herein, other moieties having the prefix "substituted" are intended to include one or more of the substituents listed above.

As used herein, the term "alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

As used herein, the term "alkynyl" refers to alkynyl groups preferably having from 2 to 10 carbon atoms and more preferably 2 to 6 carbon atoms and having at least 1 and preferably from 1–2 sites of alkynyl unsaturation.

As used herein, the term "acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

As used herein, the term "acylamino" refers to the group —C(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

As used herein, the term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

As used herein, the terms "halo" or "halogen" refer to fluoro, chloro, bromo and iodo and preferably is either fluoro or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —S$_2$-aryl, —SO$_2$-heteroaryl, trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

"Heterocycle" or "heterocyclic" refers to a monovalent saturated or unsaturated group having a single ring or multiple condensed rings, from 1 to 15 carbon atoms and from 1 to 4 hetero atoms selected from the group consisting of nitrogen, sulfur or oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, of course, that such groups do not contain any substitution or substitution patterns which are sterically impractical and/or synthetically non-feasible.

"Pharmaceutically acceptable salts" refers to pharmaceutically acceptable salts of a compound of Formulas IA, IB, or IC, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

As used herein, a "negative dromotropic effect" is a decrease in the conduction velocity of the nerve tissue in the heart. As a consequence of this slow down of the conduction velocity, the S—H interval is prolonged.

Compound Preparation

As used herein the term "amino acid" means an alpha amino acid selected from those amino acids which naturally occur in proteins but without regard for specific stereochemical properties. The term "protected amino acid" means an amino acid in which the alpha amine group has been protected with a protecting group, as defined above. The terms "amino acid residue" and "amino acid moiety" are used synonymously herein.

Certain of the compounds are sufficiently basic, (e.g., amino derivatives) or acidic (e.g., carboxylic acid derivatives) to form salts. Pharmaceutically acceptable salts of the compounds of formulas IA, IB and IC are within the scope of the present invention. As will be understood by those skilled in the art, pharmaceutically acceptable salts include, but are not limited to, salts with inorganic acids such as hydrochloride, sulfate, phosphate, hydrobromide, and nitrate or salts with an organic acid such as malate, maleate, fumarate, tartrate, succinate, citrate, acetate, lactate, methanesulfonate, p-toluenesulfonate, palmoate, salicylate, and stearate.

Compounds

The compound have the following general formulas IA, IB, and IC:

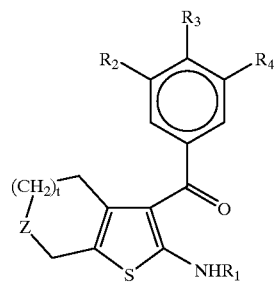
(IA)

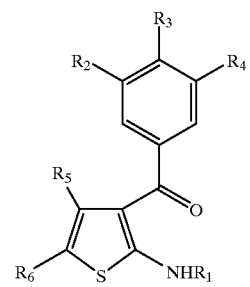
(IB)

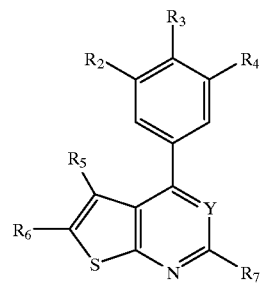
(IC)

wherein:
  $R_1$ is hydrogen, alkyl, substituted alkyl, or haloacetyl;
  $R_2$, $R_3$, and $R_4$ are independently hydrogen, halogen, alkyl, substituted alkyl, aryl, heteroaryl, heterocyclic, lower alkenyl, lower alkanoyl, amino, trifluoromethyl, amino alkyl, nitro, or cyano;
  t is 0, 1, 2, or 3;
  Z is NH, N—C(X)—NH-aryl, NC(X)—NH-alk, N—C(X)—O-alk, N—C(X)—O-alkaryl, N—C(X)—O-aryl, N(alk)$_2$ (⁺) (and an associated pharmaceutically acceptable anion such as F⁻, Cl⁻, Br⁻ or I⁻), N—(Gr)$_m$(Am)$_n$(Alk)$_p$(Ar)$_q$, or CH—(Gr)$_m$(Am)$_n$(Alk)$_p$(Ar)$_q$,
    wherein
    Gr is —SO$_2$—, —C(O)O—, or —C(O)—,
    Am is —CH(NH$_2$)—, an amino acid residue, or an amino protected amino acid residue,
    Alk is hydrogen, alkylene, substituted alkylene, alkenylene or substituted alkenylene, Ar is aryl or substituted aryl, wherein the substituents include one or more alkyl or substituted alkyl groups or one or more nitro groups, m is 0 or 1, n, p, and q are independently 0, 1, or 2, provided that at least one of m, n, p, and q is other than 0;

X is O, S or N-alk, $R_5$ and $R_6$ are independently hydrogen, alkyl, substituted alkyl, or taken together form a lower alkenyl ring of 5 or 6 members, provided that if $R_2$, $R_3$, and $R_4$ are hydrogen, then, both $R_5$ and $R_6$ may be neither hydrogen nor methyl;

further provided that if $R_2$ and $R_3$ are hydrogen while $R_4$ is trifluoromethyl or if $R_2$ and $R_4$ are hydrogen while $R_3$ is chloro, then both $R_5$ and $R_6$ may not be methyl;

$R_7$ is hydrogen, alkyl, N(alk)$_2$, substituted alkyl or OH (and the resulting tautomeric form in which the OH is tautomerized to a carbonyl and the imine is tautomerized to an NH group);

Y is nitrogen, CH, C—CN or C—C(O)OR$_8$; and wherein $R_8$ is hydrogen, alkyl or substituted alkyl.

Particular compounds include compounds of formulas IA, IB, and IC wherein:

$R_1$ is hydrogen, $R_2$, $R_3$, and $R_4$ are independently hydrogen, halogen, or trifluoromethyl, t is 0, 1, 2, or 3, Z is NH, N—(CH$_2$)$_{1-3}$ phenyl, N-(ethoxycarbonylmethyl), N-(2-t-butoxycarbonylamino-3 -(4-hydroxyphenyl)-propion-1-yl), N-(3-methylbut-2-en-1-yl), N-(4-methylphenylsulfonyl), N-(4-nitro-(2-phenyleth-1-yl), or N-(benzyloxycarbonyl);

$R_5$ and $R_6$ are both hydrogen or both methyl, or $R_5$ and $R_6$ together form a cyclopentyl or cyclohexyl ring;

$R_7$ is hydrogen or methyl;

$R_8$ is ethyl.

Specific compounds are:

| Compound/ Example Number | Compound Name |
|---|---|
| 2 | (2-amino-4,5-dimethyl-3-thienyl)-[(3,5-dichloro-4-amino)-phenyl)]methanone, |
| 5 | (2-amino-3-thienyl)-(4-chlorophenyl)methanone, |
| 7 | 2-amino-3-benzoyl-6-benzyloxycarbonyl-4,5,6,7-tetrahydrothieno[2,3-c]pyridine, |
| 8 | 2-amino-3-benzoyl-4,5,6,7-tetrahydrothieno[2,3-c]pyridine, |
| 9 | 2-amino-3-(4-chloro-benzoyl)-6-benzyloxycarbonyl-4,5,6,7-tetrahydrothieno[2,3-c]pyridine, |
| 10 | 2-amino-3-(4-chloro-benzoyl) 4,5,6,7-tetrahydrothieno[2,3-c]pyridine, |
| 11 | 2-amino-3-[3-(trifluoromethyl)-benzoyl]-6-(3-phenylprop-1-yl)-4,5,6,7-tetrahydrothieno[2,3-c]pyridine, |
| 13 | 2-amino-3-[3-(fluoromethyl)-benzoyl]-6-(phenylmethyl)-4,5,6,7-tetrahydrothieno[2,3-c]pyridine, |
| 14 | 2-amino-3-(4-chloro-benzoyl)-6-(2-phenyleth-1-yl)-4,5,6,7-tetrahydrothieno[2,3-c]pyridine, |
| 15 | 2-amino-3-[3-(fluoromethyl)-benzoyl]-6-(2-phenyleth-1-yl)-4,5,6,7-tetrahydrothieno[2,3-c]pyridine, |
| 16 | 2-amino-3-(4-chloro-benzoyl)-6-(3-phenylprop-1-yl)-4,5,6,7-tetrahydrothieno[2,3-c]pyridine, |
| 18 | 2-amino-3-(4-chloro-benzoyl)-6-(ethoxycarbonylmethyl)-4,5,6,7-tetrahydrothieno[2,3-c]pyridine, |

| Compound/ Example Number | Compound Name |
|---|---|
| 20 | 2-amino-3-benzoyl-6-(3-methylbut-2-en-yl)-4,5,6,7-tetrahydrothieno[2,3-c]pyridine, |
| 21 | 2-amino-3-(4-chloro-benzoyl)-6-[4-nitro-(2-phenyleth-1-yl)]-4,5,6,7-tetrahydrothieno[2,3-c]pyridine, |
| 22 | 2-amino-3-benzoyl-6-[4-nitro-(2-phenyleth-1-yl)]-4,5,6,7-tetrahydrothieno[2,3-c]pyridine, |
| 23 | 2-amino-3-benzoyl-6-[2-t-butoxycarbonylamino-3-(4-hydroxyphenyl)-propion-1-yl]-4,5,6,7-tetrahydrothieno[2,3-c]pyridine, |
| 24 | 2-amino-3-benzoyl-4,5,6,7-tetrahydrobenzo[b]thiophene, |
| 25 | 4-phenyl-5,6,7,8-tetrahydro[1]Benzothieno[2,3-d]pyrimidine |
| 26 | 2-methyl,3-ethoxycarbonyl-4-phenyl-5,6,7,8-tetrahydro[1]Benzothieno[2,3-b]pyridine |
| 27 | 2-Amino-3-(4-bromobenzoyl)-cyclopenta[b]thiophene |
| 28 | 2-amino-3-benzoyl-6-(4-methylphenylsulphonyl)-4,5,6,7-tetrahydrothieno[2,3-c]pyridine |
| 29 | 2-amino-3-(4-chlorobenzoyl)-6-(((phenyl)amino)carbonyl)-4,5,6,7-tetrahydrothieno(2,3-c)pyridine |
| 30 | 2-amino-3-(4-chlorobenzoyl)-6-(3-methyl-but-2-en-1-yl)-4,5,6,7-tetrahydrothieno(2,3-c)pyridine |
| 31 | 2-amino-3-(4-chlorobenzoyl)-6-prop-2-en-1-yl)-4,5,6,7-tetrahydrothieno(2,3-c)pyridine |
| 32 | 2-amino-3-(4-iodobenzoyl)-6-(((phenyl)amino)carbonyl)-4,5,6,7-tetrahydrothieno(2,3-c)pyridine |
| 33 | 2-amino-3-(4-bromobenzoyl)-6-(((phenyl)amino)carbonyl)-4,5,6,7-tetrahydrothieno(2,3-c)pyridine |
| 34 | 2-amino-3-(4-bromobenzoyl)-4,5,6,7-tetrahydrothieno(2,3-c)pyridine |
| 35 | 2-amino-3-(4-bromobenzoyl)-6-(3-methyl-but-2-en-1-yl)-4,5,6,7-tetrahydrothieno(2,3-c)pyridine |
| 36 | 2-amino-3-(4-bromobenzoyl)-6-(prop-2-en-1-yl)-4,5,6,7-tetrahydrothieno(2,3-c)pyridine |
| 37 | 2-amino-3-(4-iodobenzoyl)-4,5,6,7-tetrahydrothieno(2,3-c)pyridine |
| 38 | 2-amino-3-(4-iodobenzoyl)-6-(3-methyl-but-2-en-1-yl)-4,5,6,7-tetrahydrothieno(2,3-c)pyridine |
| 39 | 2-amino-3-(4-phenylbenzoyl)-6-(benzyloxycarbonyl)-4,5,6,7-tetrahydrothieno(2,3-c)pyridine |
| 40 | 2-amino-3-(4-phenylbenzoyl)-6,6-bis(3-methyl-but-2-en-1-yl)-4,5,6,7-tetrahydrothieno(2,3-c)pyridinium chloride |
| 41 | 2-amino-3-(4-fluorobenzoyl)-6-(benzyloxycarbonyl)-4,5,6,7-tetrahydrothieno(2,3-c)pyridine |
| 42 | 2-amino-3-(4-phenylbenzoyl)-4,5,6,7-tetrahydrothieno(2,3-c)pyridine |
| 43 | 2-amino-3-(4-phenylbenzoyl)-6,6-bis(prop-2-en-1-yl)-4,5,6,7-tetrahydrothieno(2,3-c)pyridinium chloride |
| 44 | 2-amino-3-cyano-4-phenyl-5,6,7,8-tetrahydro(1)benzo-thieno(2,3-b)pyridine; and |
| 45 | 2-hydroxy-3-cyano-4-phenyl-5,6,7,8-tetrahydro(1)benzo-thieno(2,3-b)pyridine |

Preparation of the Compounds

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amine group converted to an amide or carbamate. Methods of protecting and de-protecting, also known as "blocking" and "de-blocking," are well known and widely practiced in the art, e.g., see T. Green, *Protective Groups in Organic Synthesis*, John Wiley, New York (1981) or *Protective Groups in Organic Chemistry*, Ed. J. F. W. McOmie, Plenum Press, London (1973).

SCHEME 1

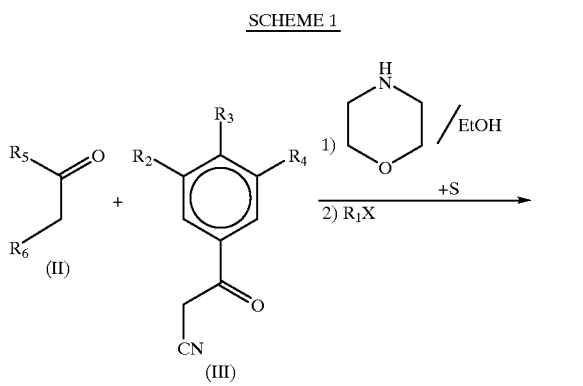

Compounds of formula IB may be conveniently prepared according to Scheme 1.

In Step 1 a compound of formula (II) is reacted with a compound of formula (III) in the presence of morpholine and molecular sulfur in a protic solvent, such as ethanol, at about 50° to about 65° C. for about an hour to yield a compound of formula IA wherein R1 is hydrogen.

Compounds of formula (IA) wherein $R_1$ is other than hydrogen may be prepared according to Step 2 by reacting a compound of formula (IB) from Step 1, wherein $R_1$ is hydrogen, with $R_1X$ (wherein $R_1$ is other than hydrogen, and X is a leaving group). For a discussion of nucleophilic displacement reactions and leaving groups, see standard organic chemistry texts such as J. March, *Advanced Organic Chemistry*, Chapter 10, John Wiley & Sons, New York (1985). Compounds of formula (II) are commercially available or may be prepared by methods known to those of skill in the art. Compound of formula (III), benzophenone derivatives, may be prepared by methods known to those of skill in the art or conveniently according to Scheme 2.

SCHEME 2

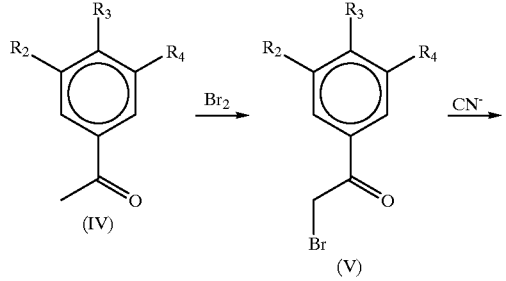

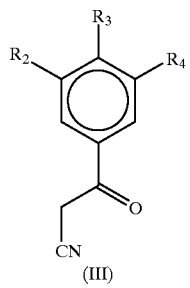

In Scheme 2, a compound of formula (IV), a substituted acetophenone, is alpha brominated with molecular bromine in a protic, polar solvent, such as acetic acid to yield the corresponding alpha bromo compound of formula (V). The compound of formula (III) is produced by reacting the compound of formula (V) with a source of cyanide ions, such as sodium or potassium cyanide, in a polar solvent, such as water, ethanol, or a mixture thereof.

SCHEME 3

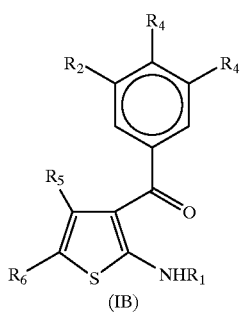

As shown in Scheme 3, a compound of formula ($IA_1$) wherein Z is NH may be prepared by hydrolyzing the CO—N urethane linkage of a compound of formula (VI) under acidic conditions, e.g., hydrogen bromide in acetic acid.

In turn, a compound of formula (VI) may be prepared in a similar manner as the reaction of Scheme 1 by substituting a compound of formula (II) with a corresponding amount of a compound of formula (VII). It may be necessary to protect the carbonyl group

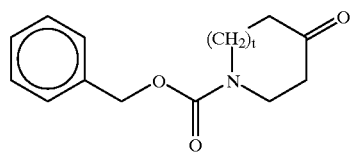

(VII)

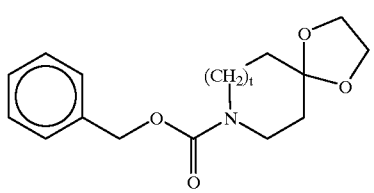

(VIII)

of the piperidinone moiety during the synthesis of a precursor compound, e.g., by converting it to an ethylenedioxy derivative as seen in formula (VIII). The protecting or blocking group is removed after the synthesis of a compound of formula (VIII) to generate a compound of formula (VII).

Compounds of formula (IA) wherein Z is a substituted nitrogen, i.e., N—$(Gr)_m(Am)_n(Alk)_p(Ar)_q$, may be prepared by nucleophilic displacement by reacting a compound of the formula X—$(Gr)_m(Am)_n(Alk)_p(Ar)_q$, wherein X is a leaving group (see March, supra), in a polar solvent in the presence of a weak base such as sodium or potassium carbonate or a tertiary amine.

SCHEME 4

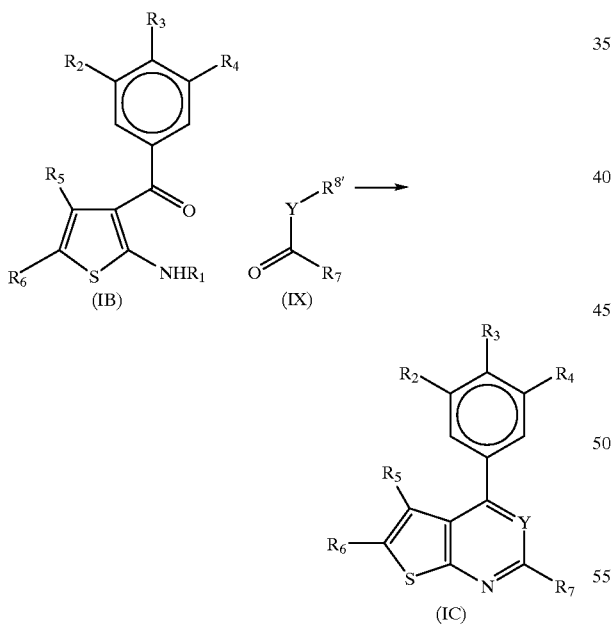

According to Scheme 4, a compounds of formula (IC), can be prepared from the corresponding compound of formula (IB), wherein $R_1$ is hydrogen, by reacting with a compound of formula (IX) in a protic, polar solvent, such as ethanol, in the presence of a strong base such as sodium ethoxide to form the pyridine moiety. (If Y is nitrogen, then $R_8'$ is $H_2$, and if Y is CH, then $R_8'$ is —$C(O)OR_8$). This reaction can conveniently be carried out by mixing the reactants, solvent and base at about 0° C. followed by heating at reflux for about 10 hours. A compound of formula (IC) wherein Y is nitrogen, i.e., $R_8$ is $H_2$, can be prepared from the corresponding compound of formula (IB) by reaction with a compound of formula $R_7$—$C(O)NH_2$, e.g., formamide, if $R_7$ is hydrogen, at about 180° C. for about 5 hours.

Compounds of formula (IA) wherein Z is N—$(Gr)_m(Am)_n(Alk)_p(Ar)_q$, and Am is an amino acid or an amino acid with the amino group protected, and m, p, and q are 0, may be prepared by reacting the corresponding compound wherein Z is NH with a protected derivative of an amino acid. An example of a protected amino acid is BOC-tyrosine ("BOC-Tyr-OH") wherein "BOC" is —$C(O)OC(CH_3)_3$. Preferably the reaction is run in a polar, aprotic solvent, such as dimethylformamide. Preparation of BOC derivatives of amino acids are well known in the art of protein and peptide chemistry. If desired the BOC moiety may be removed by standard means known in the art to restore the amino acid residue.

Compounds which include quaternary ammonium salts, for example, at the 6-position, can be prepared by reacting the amine at the desired position with excess alkyl halides using routine alkylation conditions. Compounds with urea linkages can be prepared by reacting the amine at the 6-position with the desired isocyanate. Urethanes can be prepared by reacting the amine at the 6-position with the desired alkyl chlorocarbonate (as shown, for example, in Morrison & Boyd, Organic Chemistry, Fourth Edition, Allyn & Bacon, Inc., Boston, 1983, page 840).

Methods of Using the Compounds

The compounds can be used for:

Protection against hypoxia and/or ischemia induced injuries (e.g., stroke, infarction);

Treatment of adenosine-sensitive cardiac arrhythmias;

antinociception (i.e., analgesics);

anticonvulsants;

cardioprotection, short term (e.g., prior to percutaneous angioplasty (PTDA), angioplasty, and cardiac surgeries) and long term (prevention of myocardial infarction, especially in high risk patients, reduction of infarct damage, especially in high risk patients);

treatment of congestive heart failure;

neuroprotection: stroke prevention, stroke treatment, treatment of Alzheimer's disease and treatment of epilepsy;

pain management generally, including different forms of neuropathic pain, e.g., diabetic neuropathy, post herpetic neuralgia;

antilipid uses: reduction of free fatty acids, triglycerides, glucose;

adjunct therapy in diabetes, including insulin and non-insulin dependent diabetes mellitus: stimulation of insulin secretion from the pancreas, increase in tissue sensitivity to insulin;

treatment of GI disorders such as diarrhea, irritable bowel disease, irritable bowel syndrome, irritable bladder, incontinence such as urge incontinence;

treatment of glaucoma;

treatment of sleep diorders, such as sleep apnea;

treatment of cardiac disarrythmias (paroxysmal supraventricular tachycardia;

use in combination with anesthesia for post surgical pain;

treatment of inflammation;

diagnostic uses, for example, to determine the presence of one or more of the above described medical conditions, or in a screening assay to determine the effectiveness of other compounds for binding to the A1 Ado receptor (i.e., through competitive inhibition as determined by various binding assays); and Other indications for which $A_1$AdoR agonists are used.

The compounds can be administered via any medically acceptable means. Suitable means of administration include oral, rectal, topical or parenteral (including subcutaneous, intramuscular and intravenous) administration, although oral or parenteral administration are preferred.

The amount of the compound required to be effective as an allosteric modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 $\mu$g/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 220 mg per day, and a typical dose would be about 150 mg per day. If discrete multiple doses are indicated, treatment might typically be 50 mg of a compound given 3 times per day.

Formulations

The compounds described above are preferably administered in formulation including an active compound, i.e., a compound of formula (IA), (IB) or (IC), together with an acceptable carrier for the mode of administration. Suitable pharmaceutically acceptable carriers are known to those of skill in the art. The compositions can optionally include other therapeutically active ingredients, such as antibiotics, antivirals, healing promotion agents, anti-inflammatory agents, immunosuppressants, growth factors, antimetabolites, cell adhesion molecules (CAMs), cytotoxic agents, antibodies, vascularizing agents, anti-coagulants, and anesthetics/analgesics. The carrier must be pharmaceutically acceptable in the sense of being compatible with the other ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound of formula (I) which upon dilution with an appropriate solvent give a solution suitable for parental administration above.

For enteral administration, the compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

The compounds can also be administered locally by topical application of a solution, ointment, cream, gel, lotion or polymeric material (for example, a Pluronic™, BASF), which may be prepared by conventional methods known in the art of pharmacy. In addition to the solution, ointment, cream, gel, lotion or polymeric base and the active ingredient, such topical formulations may also contain preservatives, perfumes, and additional active pharmaceutical agents.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Bioloy and Medicine*, pp. 287–341 (Academic Press, 1979). Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925, 673 and 3,625,214, the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Determination of the Degree of Activity for the Compounds

The activity of the compounds can be readily determined using no more than routine experimentation using any of the following assays.

Binding Assays.

The prototypical allosteric enhancer PD 81,723, (prepared in Example 4; see Bruns et al., *Mole. Pharm.*, 38:939 (1990), Cao et al., *Gen Pharmac.* 26:1545 (1995), and Amoah-Apraku et al., *J. Pharm. Exper. Ther.* 266(2):611(1993)) has both enhancing and inhibitory activity at the $A_1$AdoR. Therefore, the effect of a novel series of benzoylthiophene derivatives was determined on both the agonist [$^3$H]CCPA and the antagonist [$^3$H]CPX binding to membranes prepared from CHO cells stably expressing the human $A_1$AdoR (CHO—hu$A_1$AdoR). The enhancing activity was estimated by the magnitude of the increase in [$^3$H]CCPA binding whereas the inhibitory and (or antagonistic) activity was evaluated by the potency of the benzoylthiophene derivatives to compete for the specific binding of [3H]CPX. The method used for the preparation of the membranes of CHO cells expressing hu$A_1$AdoR, and the protocols for the radioligand binding assays are described by Kollias-Baker et al., (*JPET*, 281, 761(1997) and *Circ. Res.*, 75, 961 (1994)).

Functional Assays.

In previous studies (Amoah-Apraku et al., *J. Pharmacol Exp. Ther.*, 266, 611 (1993) and Kollias-Baker, supra) the prototypical allosteric enhancer PD 81,723 was shown to selectively enhance $A_1$AdoR-mediated prolongation of the stimulus to His (S—H) bundle interval (negative dromotropic effect) but did not increase the $A_{2a}$AdoR-mediated coronary vasodilation caused by Ado. Therefore, the effect of compound 20 on the negative dromotropic action of Ado in guinea pig isolated perfused hearts was determined. The guinea pig isolated perfused heart preparation and the methods for recording His bundle electrograms and measuring the S—H intervals have been previously reported.

Results

Radioligand Binding Assays

Figure 1B:
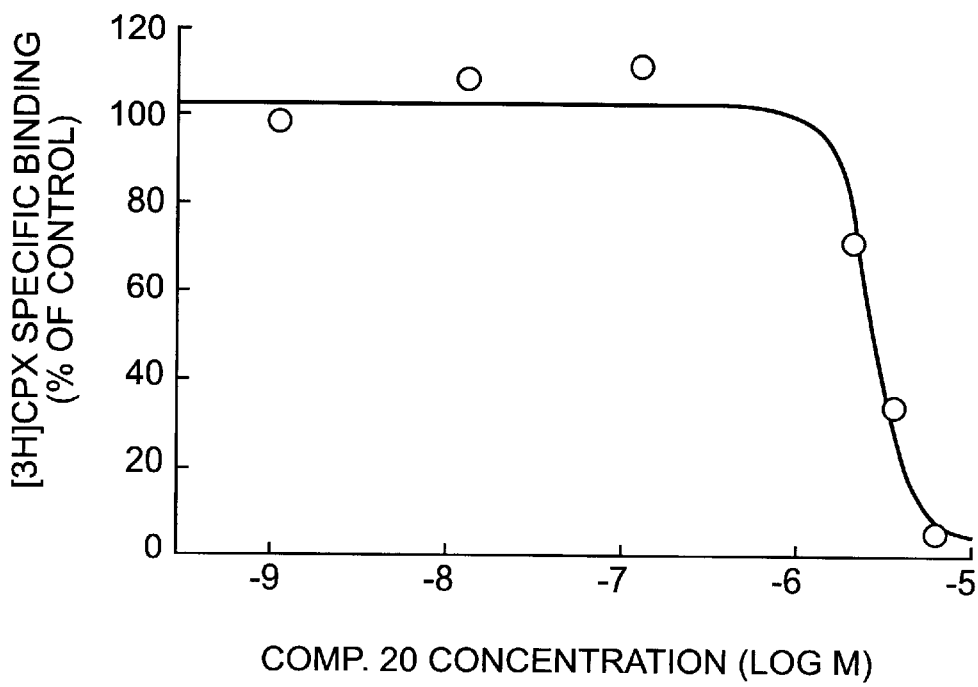
Figure 2A:
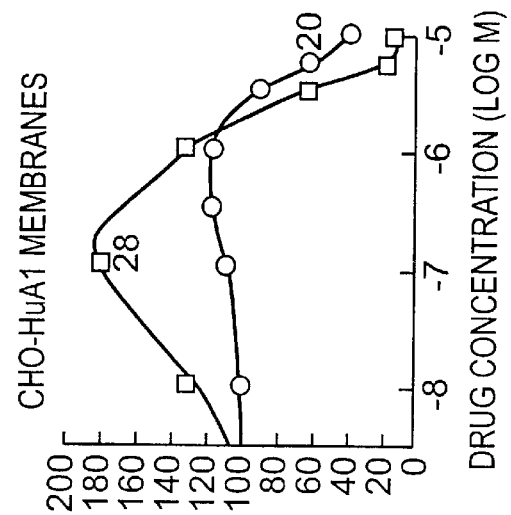
FIGS. 2A–D are graphs showing the specific binding (percent of control) of the agonist [$^3$H]2-chloro-N$^6$-cyclopentyladenosine ([$^3$H]CCPA) as a function of concentration (log M) of various allosteric enhancers.
Figure 2B:
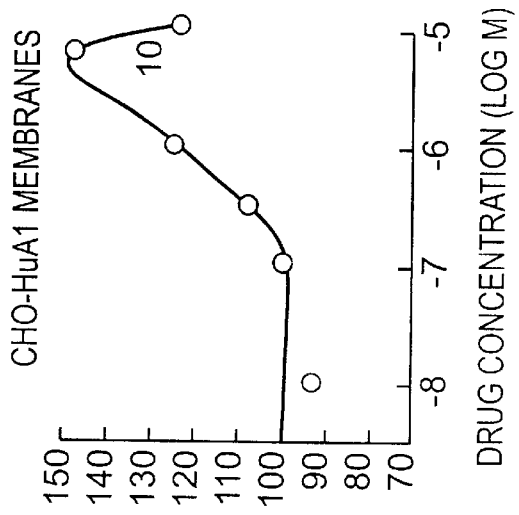
Figure 2C:
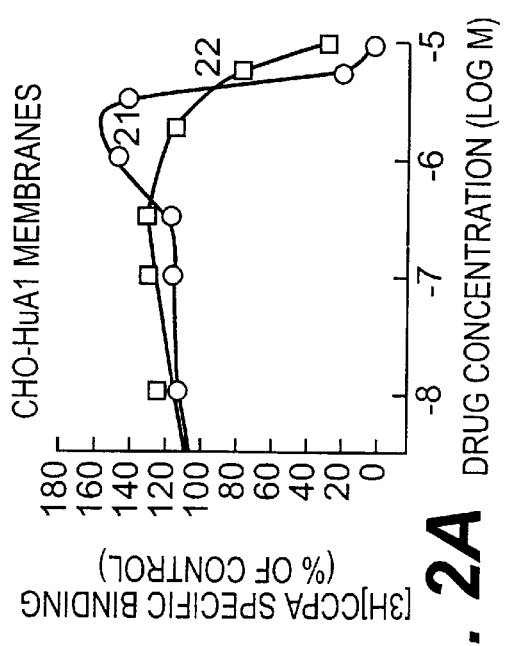
Figure 2D:
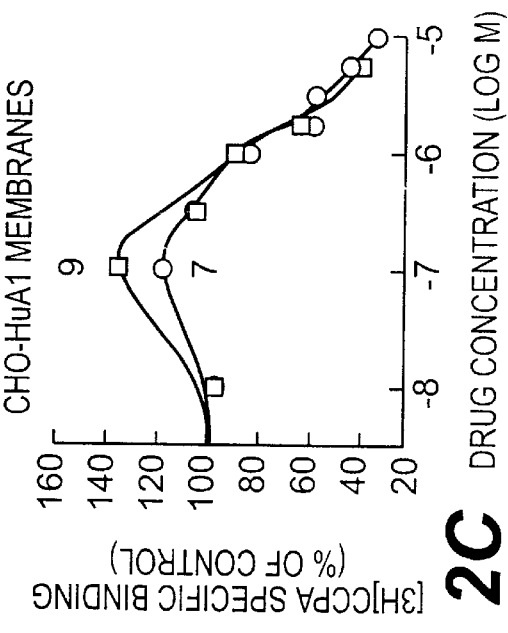
Figure 3B:
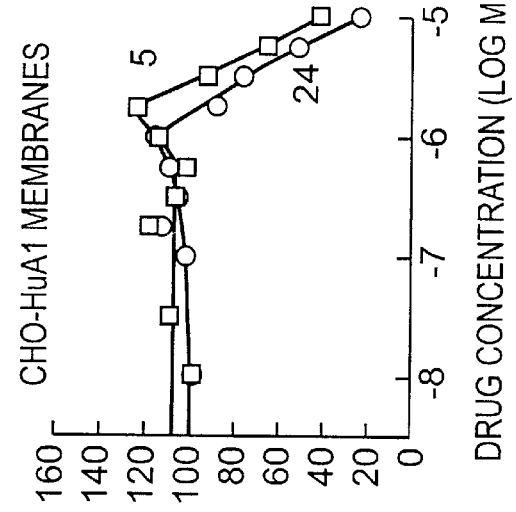
FIGS. 3A–D are graphs showing the specific binding (percent of control) of the agonist [$^3$H]2-chloro-N$^6$-cyclopentyladenosine ([$^3$H]CCPA) as a function of concentration (log M) of various allosteric enhancers.
Figure 3D:
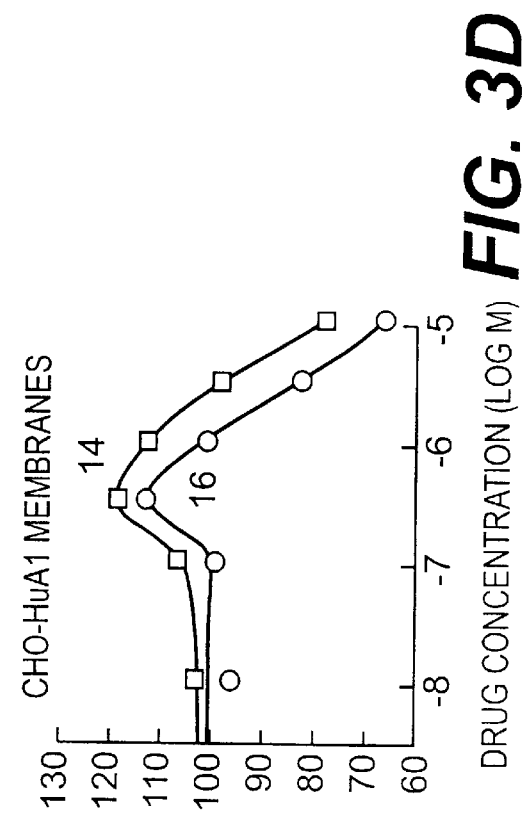
Figure 3A:
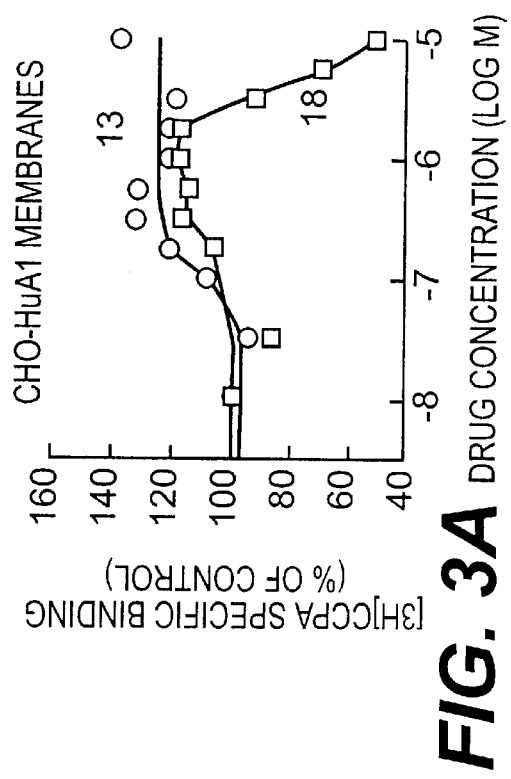
Figure 3C:
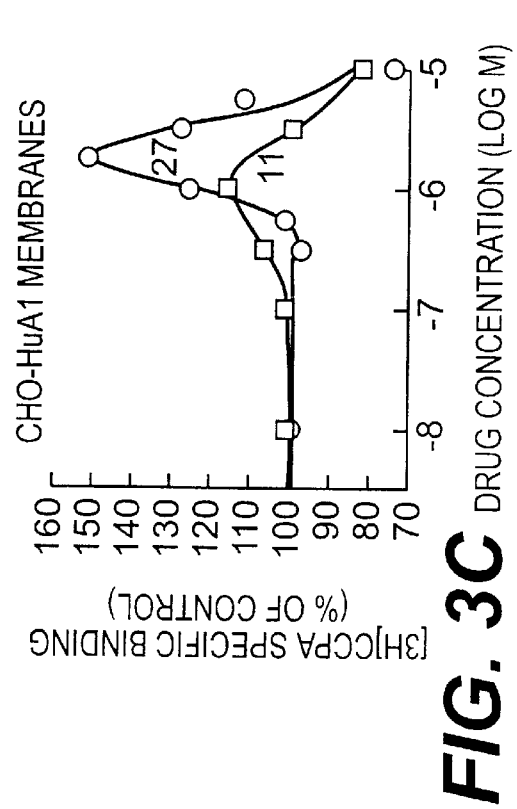

The effect of the benzoylthiophene derivative compound 20 on agonist and antagonist binding to CHO cells expressing the recombinant hu$A_1$AdoR was investigated. Specifically, the effects of compound 20 on the binding of the agonist radioligand [$^3$H]CCPA (2 nM) and the antagonist radioligand [$^3$H]CPX (1 nM) to recombinant CHO—hu$A_1$AdoR were determined. As shown in FIG. 1A, the effect of compound 20 on the specific binding of [$^3$H]CCPA was biphasic, at concentrations up to 7 µM it increased but thereafter it decreased the specific binding of [$^3$H]CCPA. In contrast, compound 20 did not enhance the binding of the antagonist radioligand [$^3$H]CPX and at concentrations greater than 1 µM decreased the specific binding of [$^3$H] CPX, see FIG. 1B. The values are mean±SEM of 4 hearts. Each data point represents mean±SEM specific binding with determinations from 2–3 experiments. FIGS. 2A–D and 3A–D are similar to FIG. 1A but show the result of [$^3$H] CCPA studies on other compounds.

Functional Studies

Figure 4A:
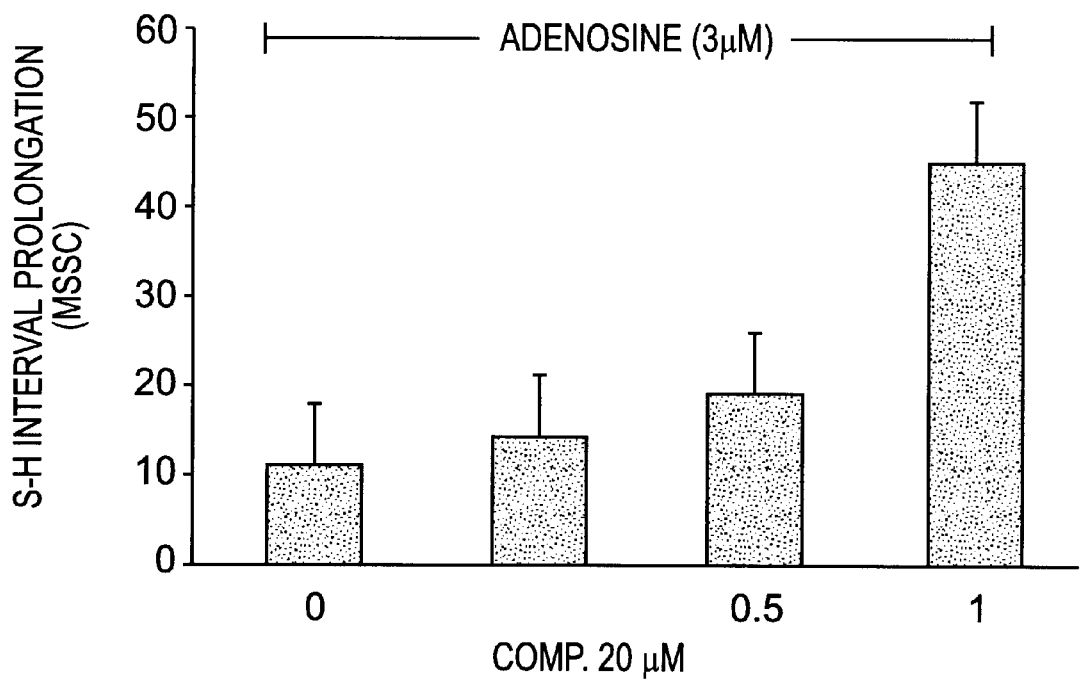
FIG. 4A is a graph showing the concentration-dependent potentiation of the negative dromotropic effect (S-H interval prolongation) of adenosine by Compound 20 in guinea pig isolated hearts as a function of time (msec) vs. concentration ($\mu$M).
Figure 4B:
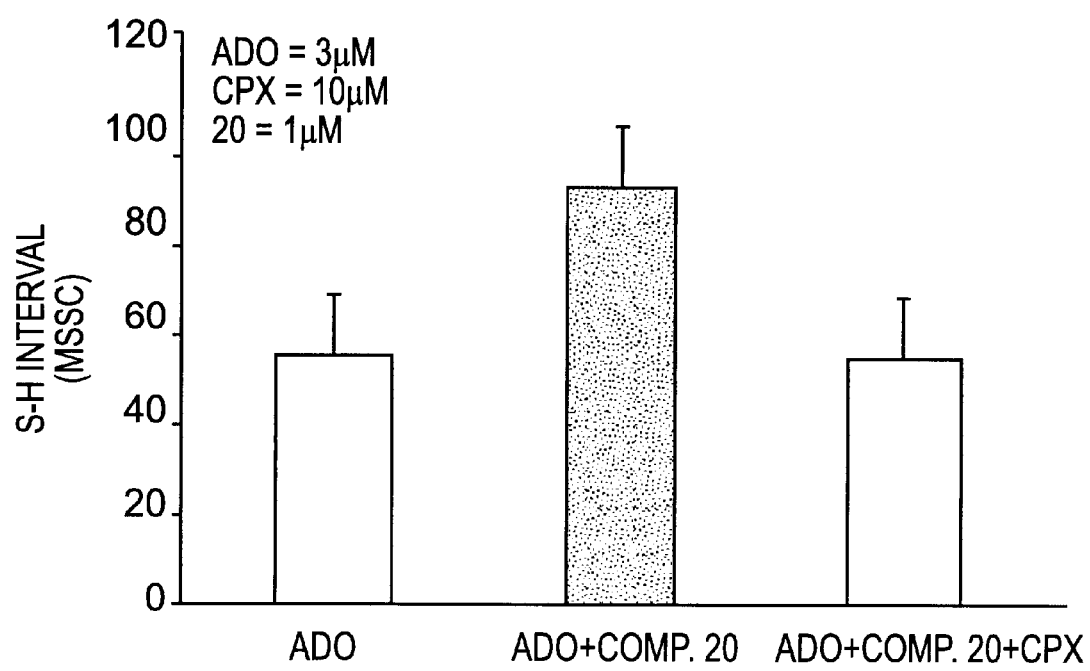
FIG. 4B is a graph showing the effect of the A$_1$AdoR antagonist CPX on the enhancement by Compound 20 of the negative dromotropic action of adenosine in guinea pig isolated hearts as a function of time (msec) vs. concentration ($\mu$M).
Figure 5:
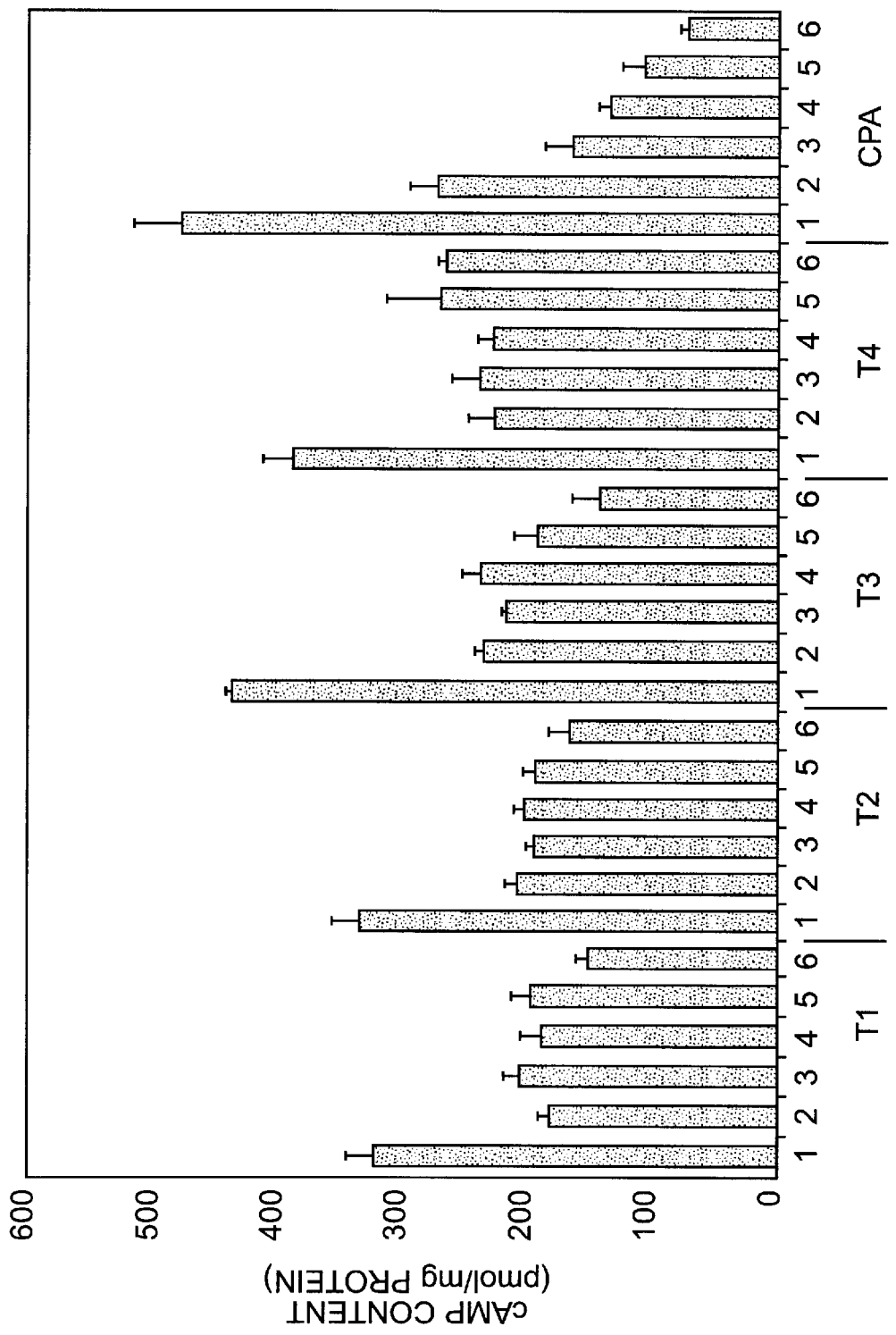
FIG. 5 is a graph showing the effect of the compounds in Examples 1–4 on the cAMP content (pmol/mg protein) of CHO cells expressing human recombinant A$_1$ adenosine receptors. Bar 1 indicates the results with no CPA. Bar 2 indicates the results with 0.1 nM CPA. Bar 3 indicates the results of 0.1 nM CPA and 0.01 $\mu$M of the tested compound. Bar 4 indicates the results of 0.1 nM CPA and 0.1 $\mu$M of the tested compound. Bar 5 indicates the results of 0.1 nM CPA and 1.0 $\mu$M of the tested compound. Bar 6 indicates the results of 0.1 nM CPA and 10 $\mu$M of the tested compound. For the CPA group, bars 1 and 2 are as described above. Bars 3–6 represent incubations with 0.3, 1, 3 and 10 nM CPA, respectively.
Figure 6:
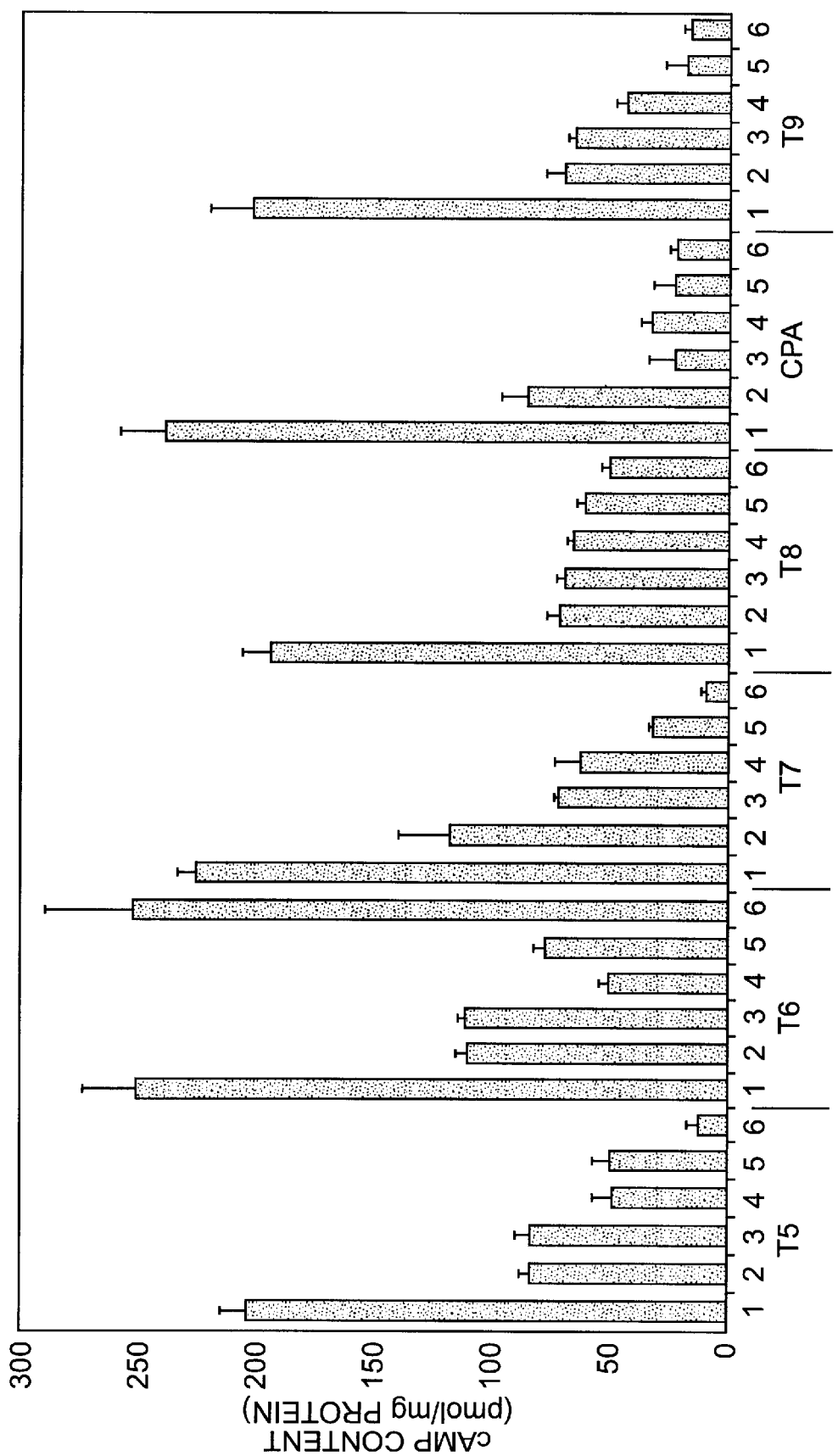
FIG. 6–10 are graphs showing the same effect as in FIG. 5, using the compounds in Examples 5–9, 10–14, 15–19, 20–24, and 25–29, respectively.
Figure 7:
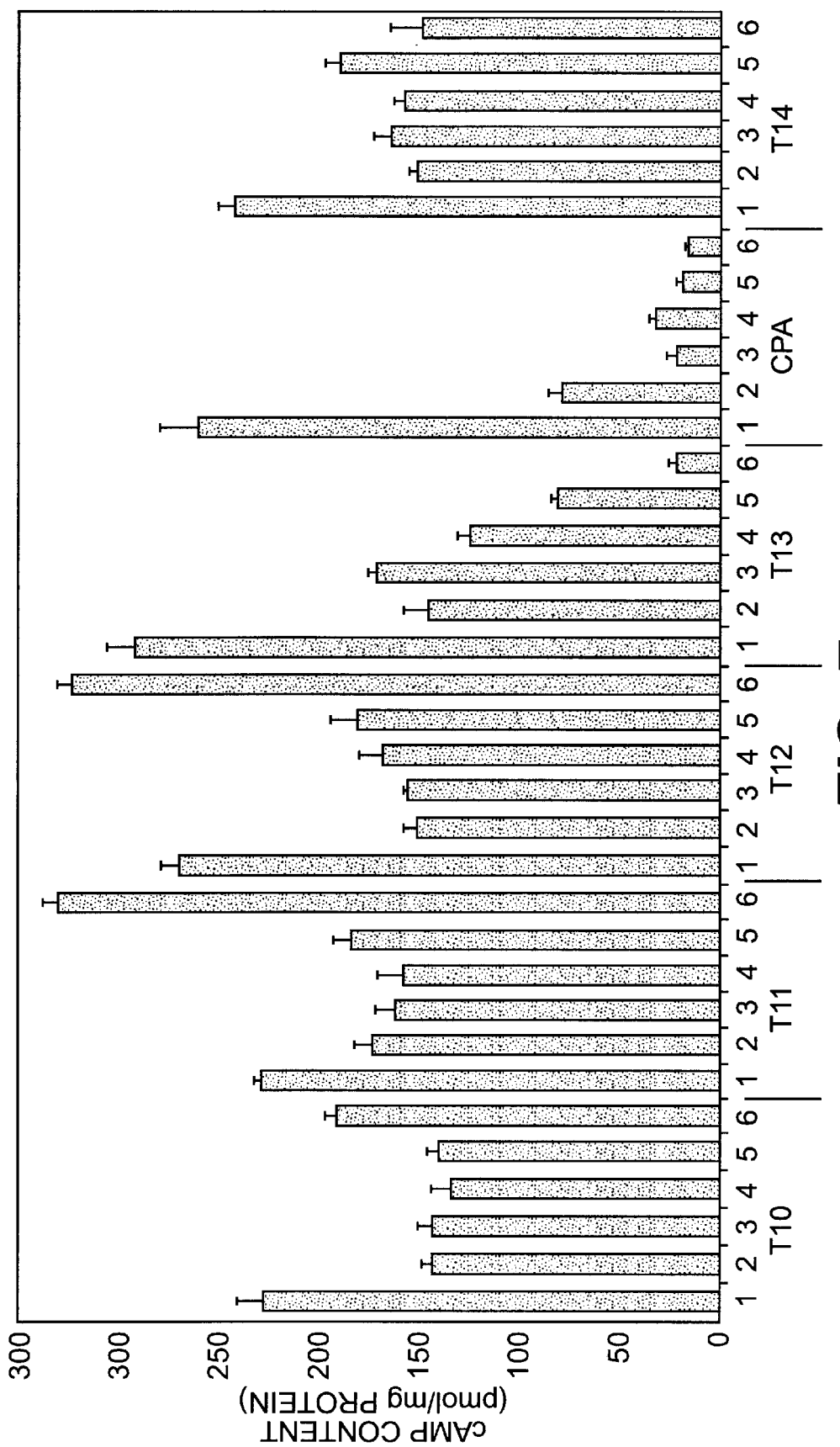
Figure 8:
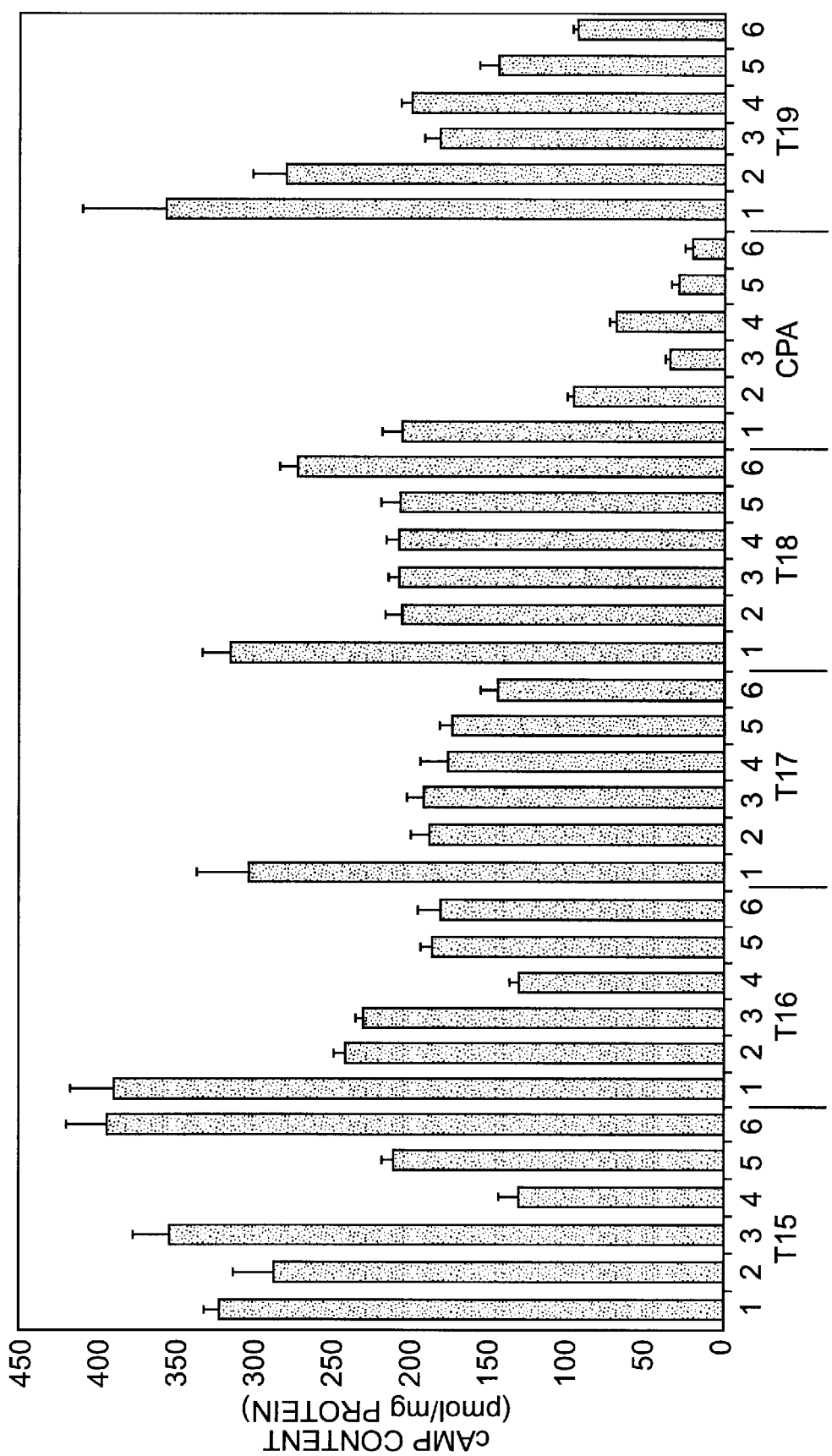
Figure 9:
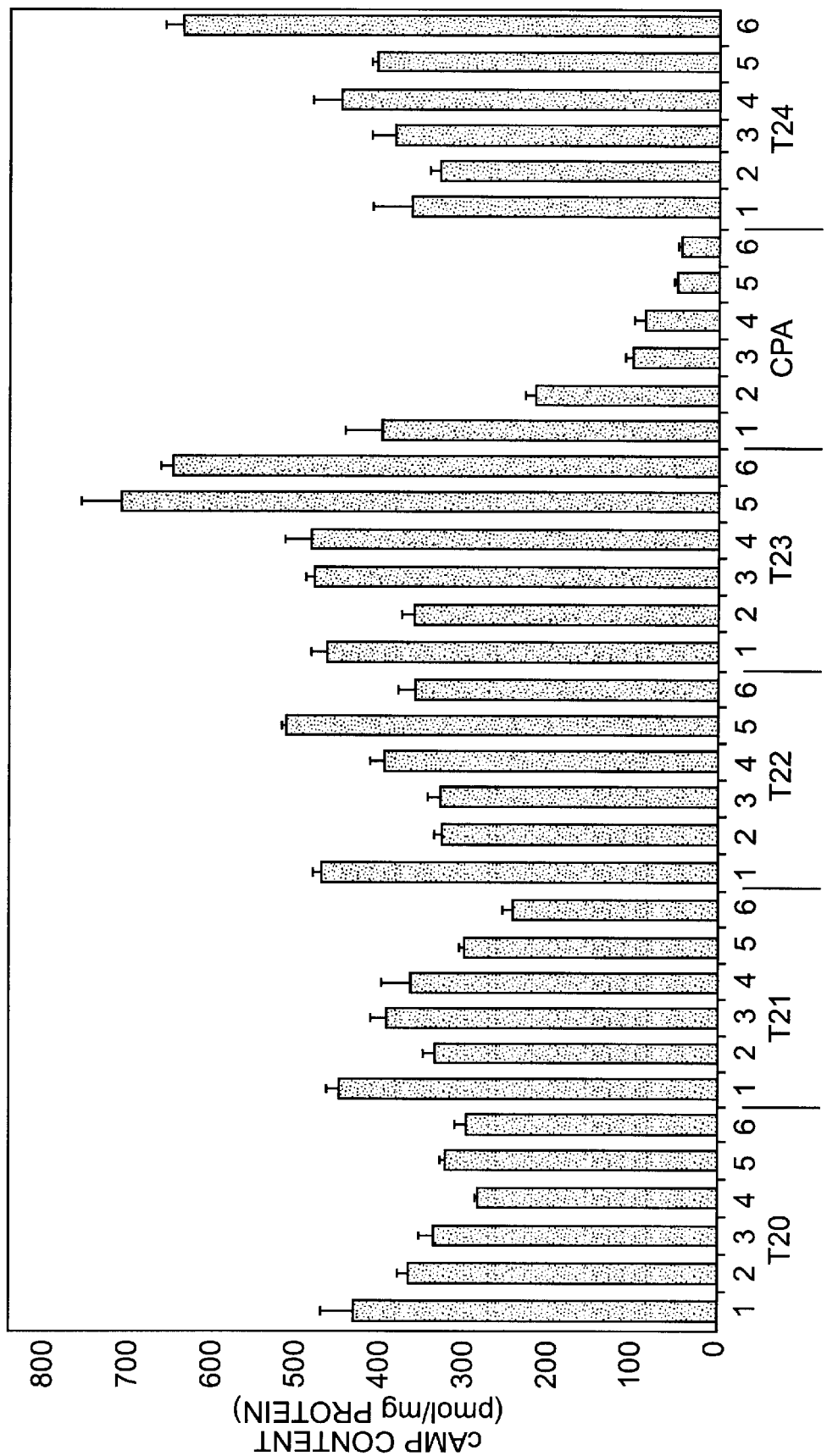
Figure 10:
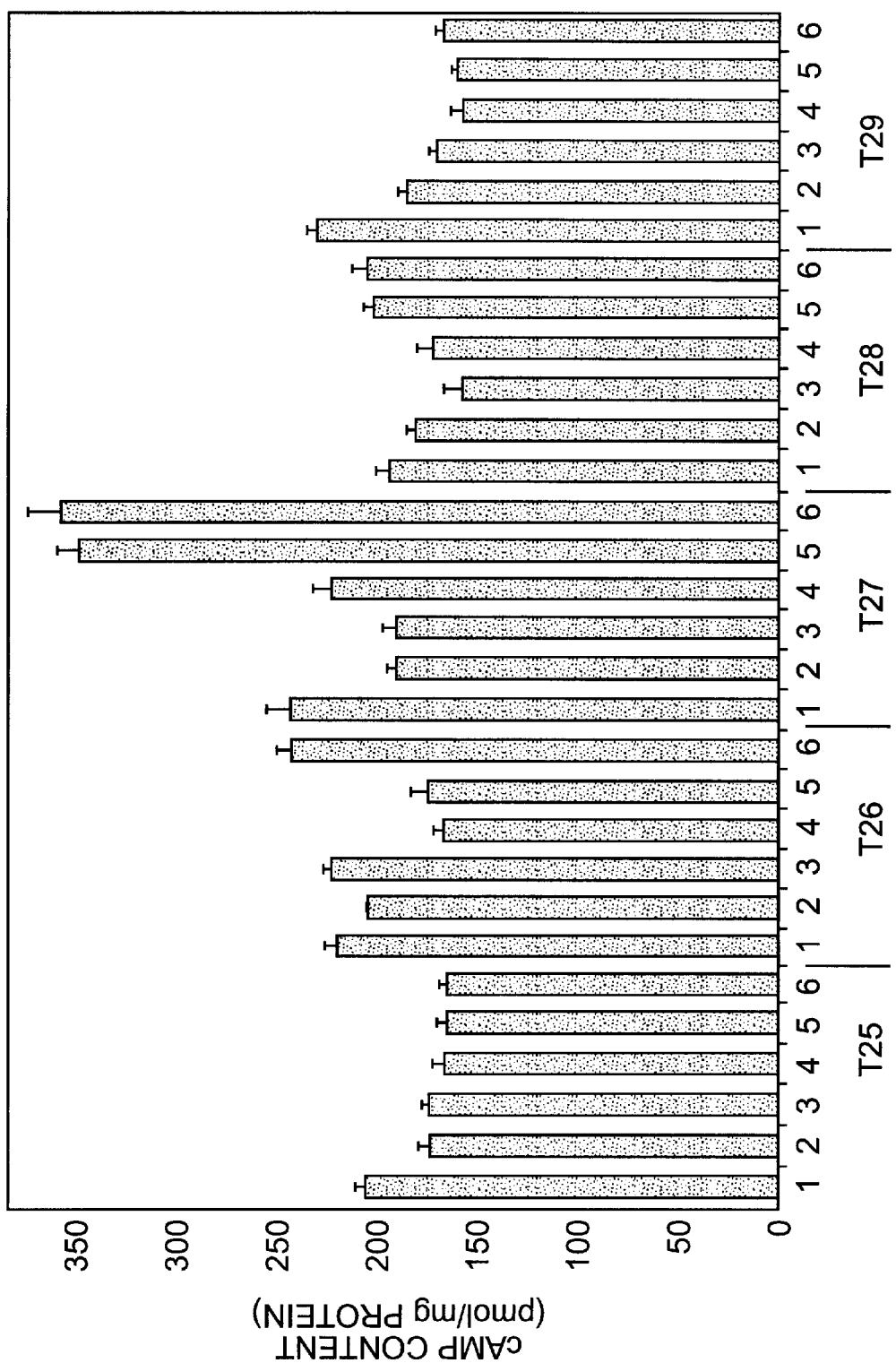
Figure 11:
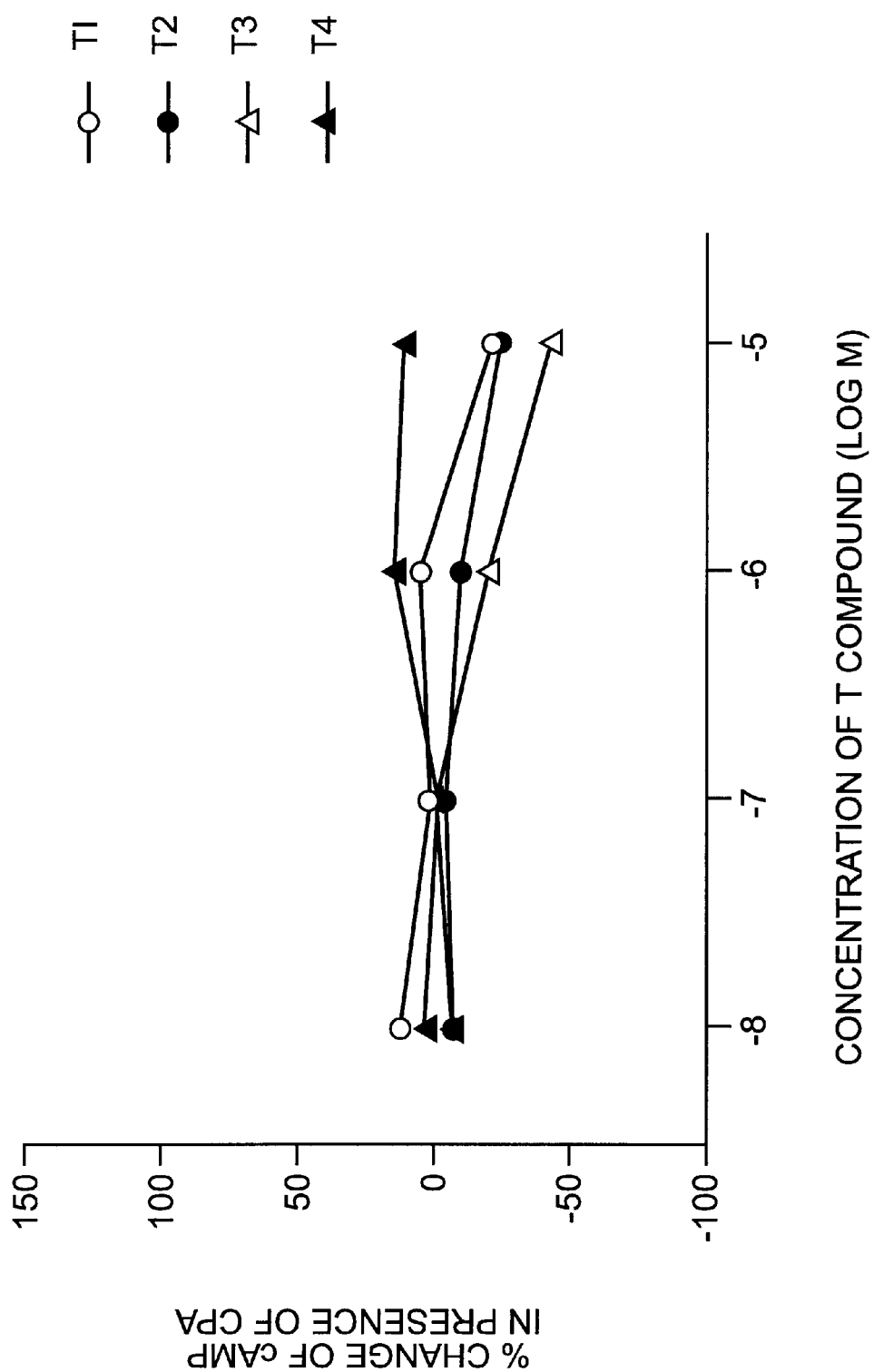
FIG. 11 is a graph showing the effect of the compounds in Examples 1–4 on the cAMP content of CHO cells in the presence of CPA, as indicated as a percent change of cAMP in the presence of CPA versus the concentration of the tested compound (log M). The data from FIG. 5 was re-plotted for this Figure.
Figure 12:
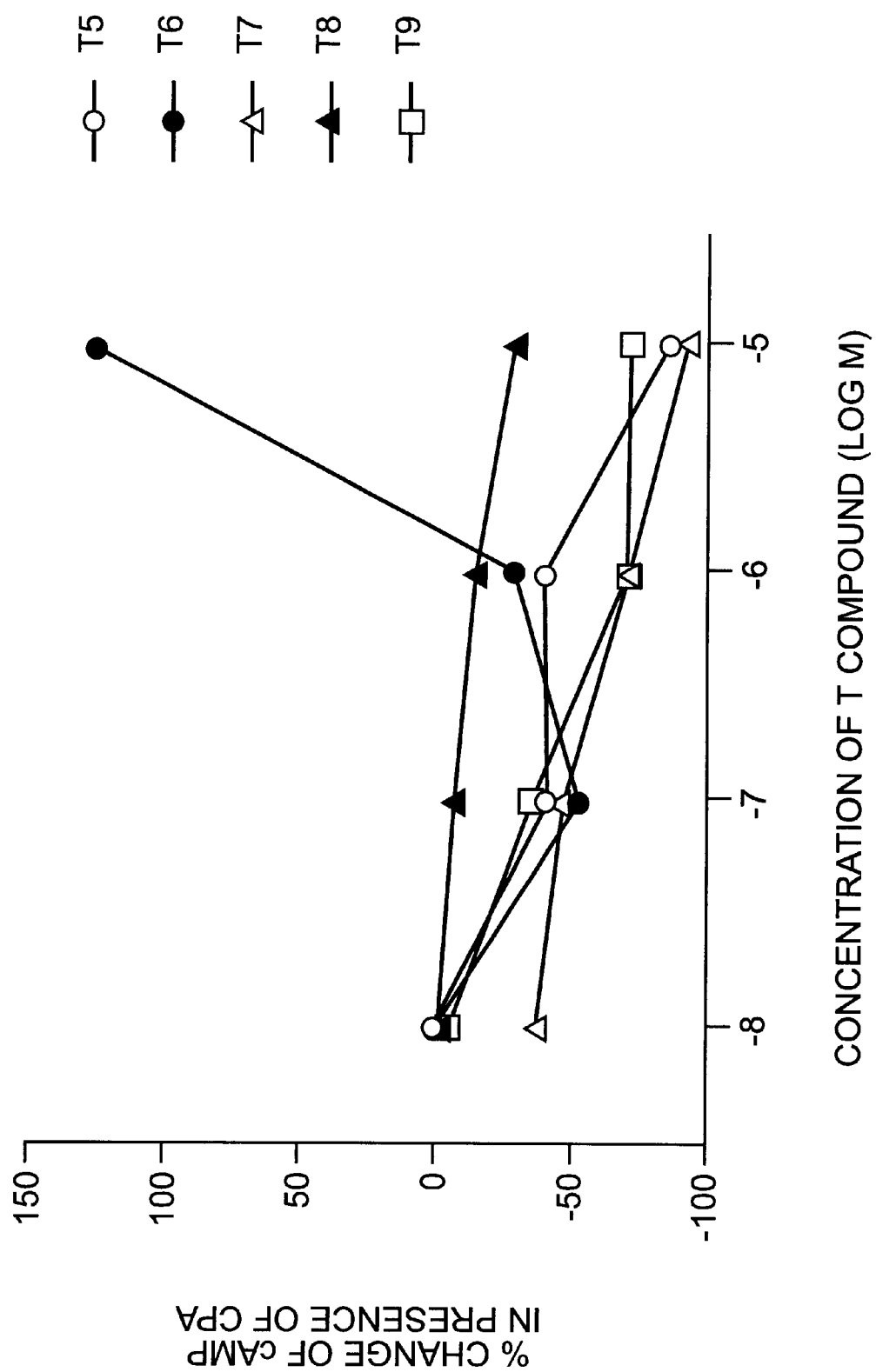
FIGS. 12–16 are graphs showing the same effect as in FIG. 11, with the data from FIGS. 6–10, respectively, re-plotted for these Figures.
Figure 13:
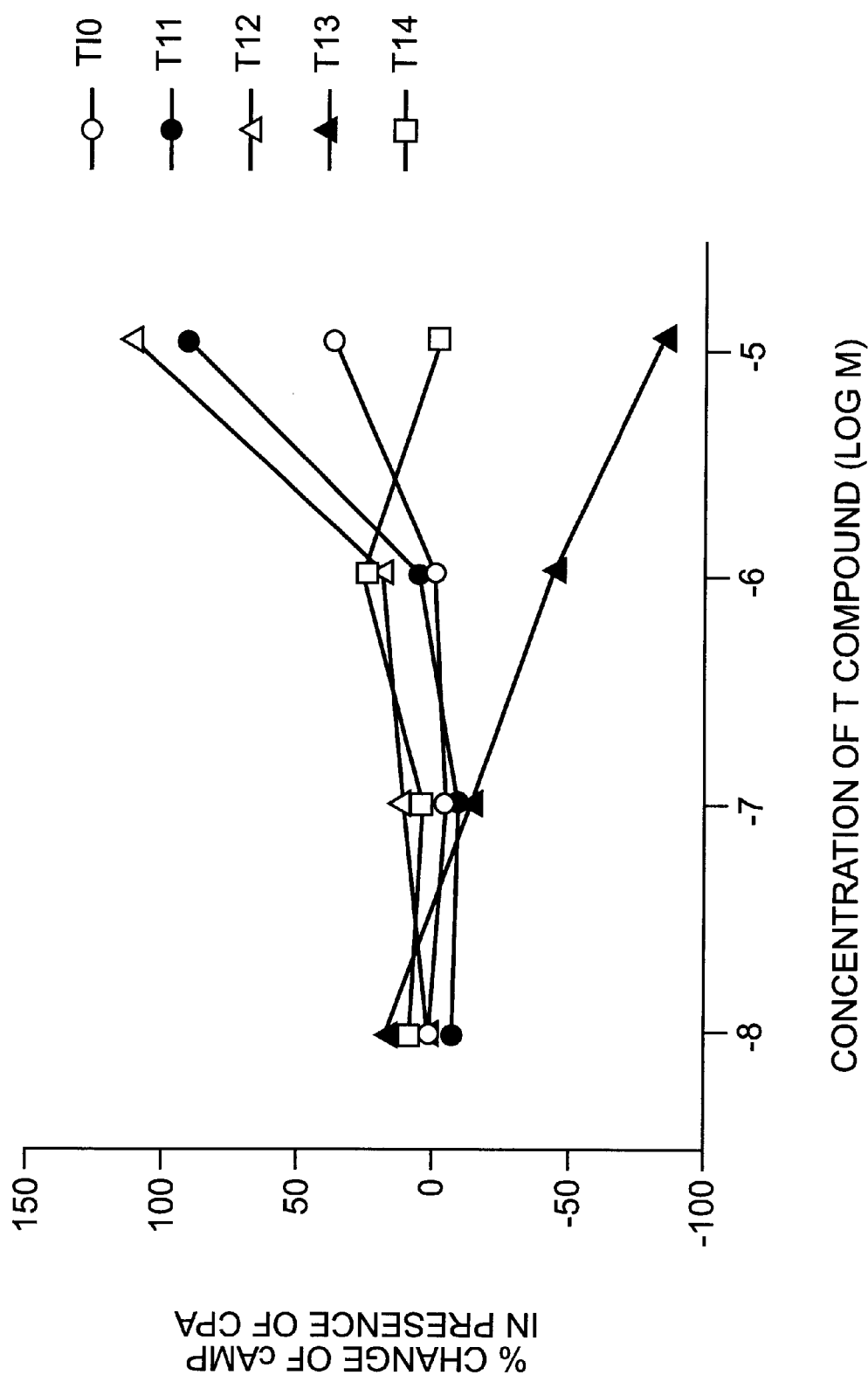
Figure 14:
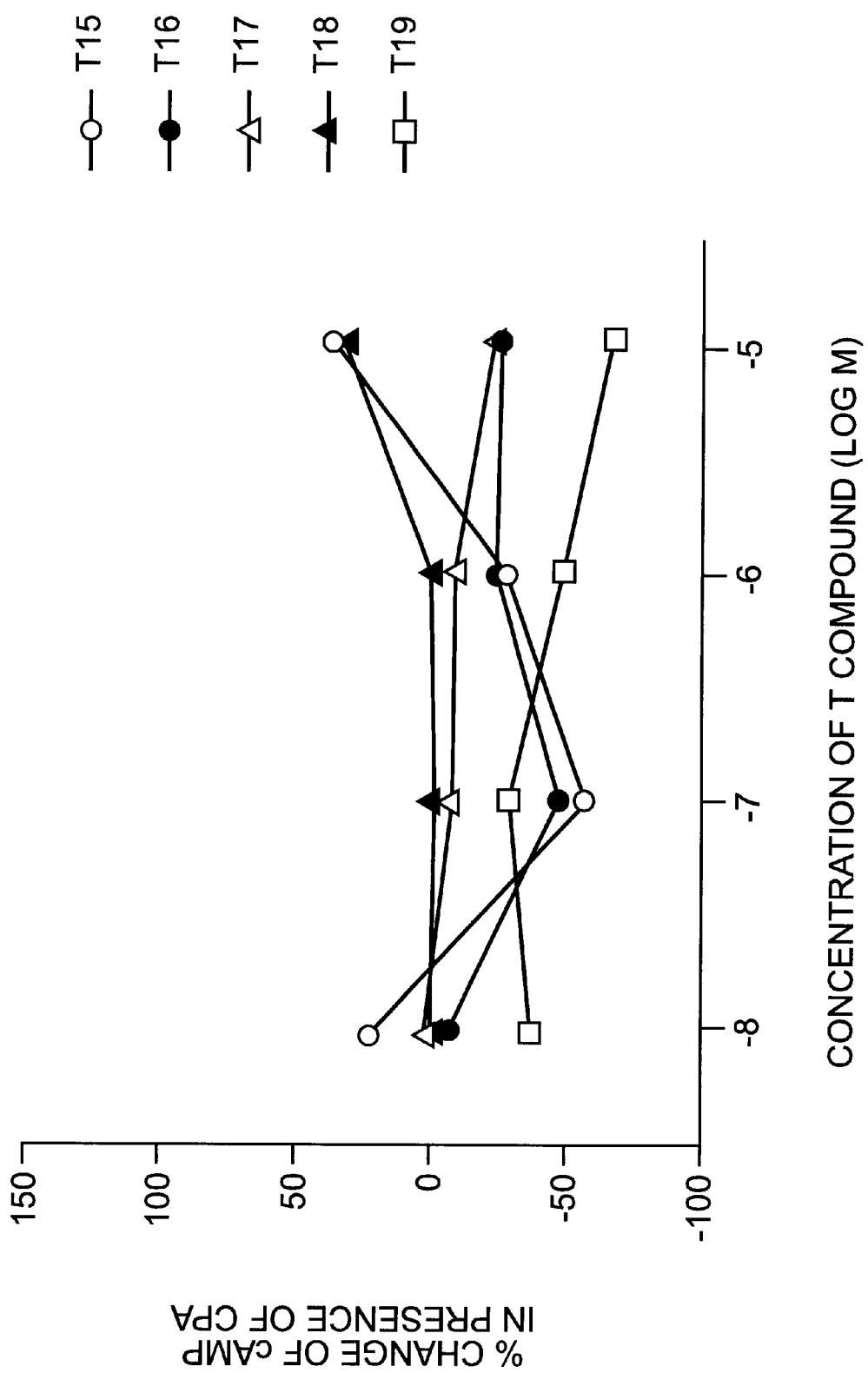
Figure 15:
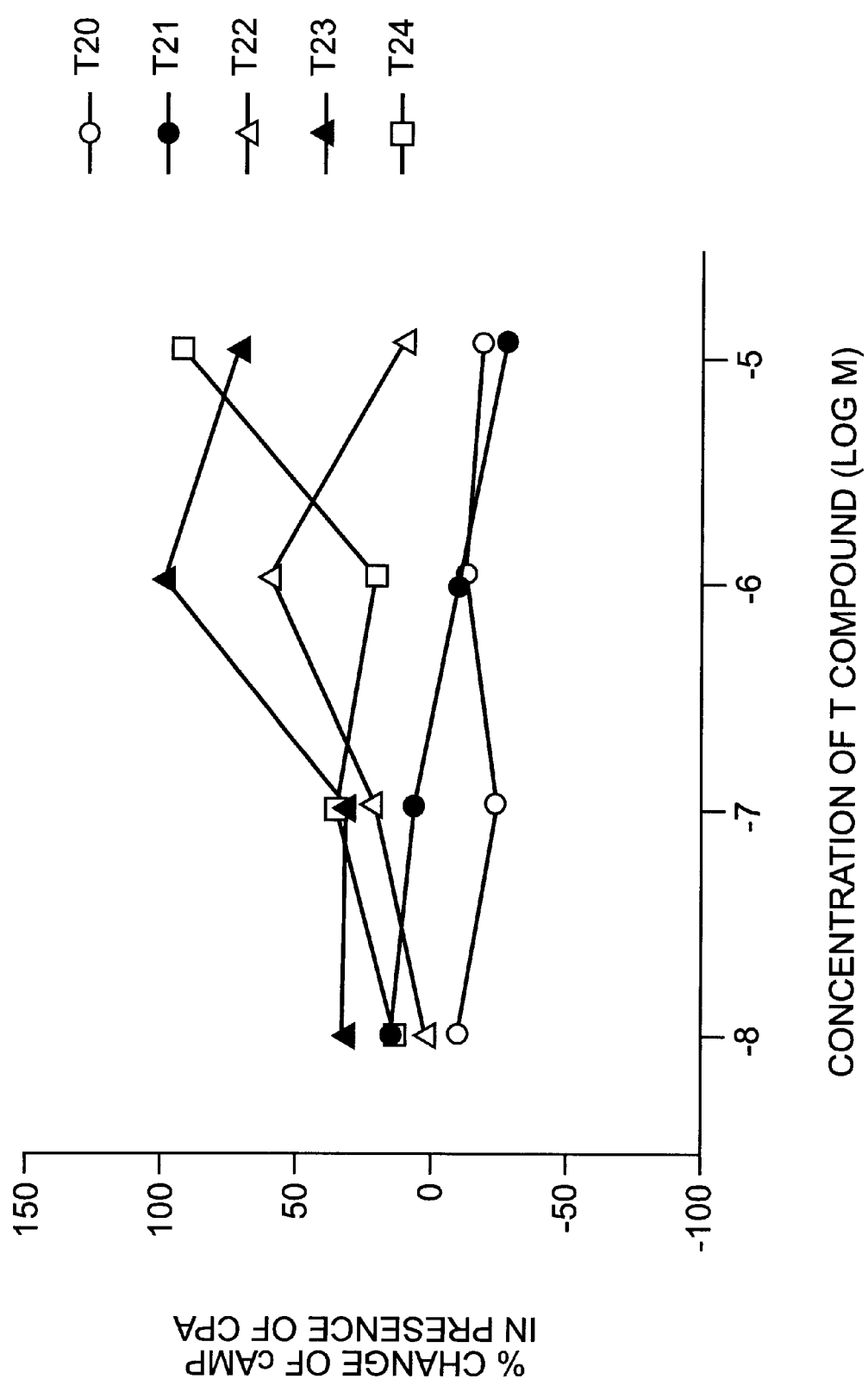
Figure 16:
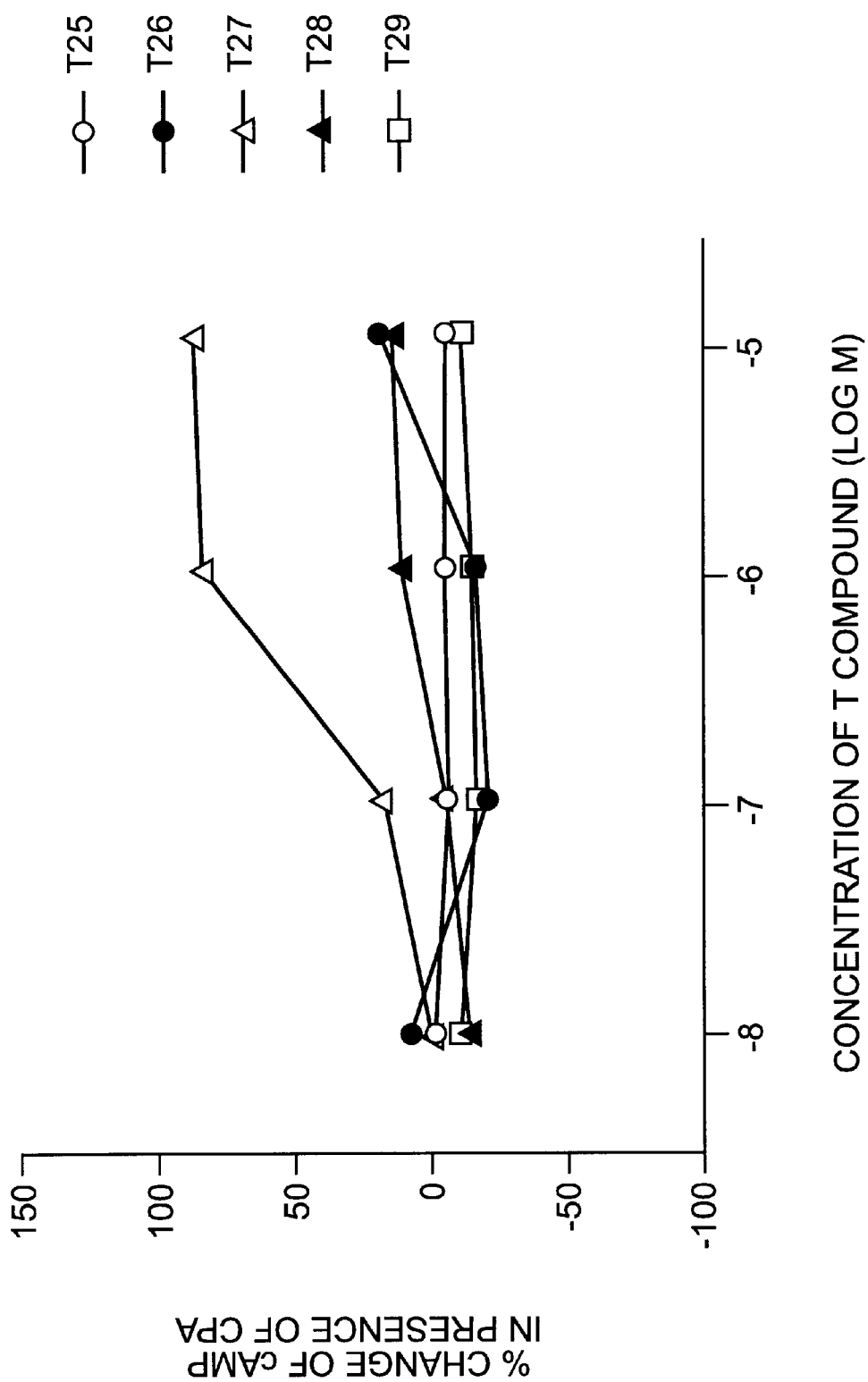

Consistent with the results of the radioligand binding assays, compound 20 enhanced the negative dromotropic effect (S—H interval prolongation) caused by Ado in a concentration-dependent manner (FIG. 4A). In pressure of 1 µM Compound 20, 3 µM adenosine caused 2° A-V block in 2 of 4 hearts. The values are mean±SEM of 4 guinea pigs. For instance, 0.1, 0.5 and 1.0 µM compound 20 enhanced the S—H prolongation induced by 3 µM Ado by 32%, 77%, and 31 1%, respectively. At 1.0 µM compound 20, the negative dromotropic effect of Ado was maximal, eliciting 2° A-V block in 2 of 4 hearts. In contrast, in the absence of compound 20, the same concentration of Ado (3 µM) prolonged the S—H interval by 11±3 msec. To demonstrate that the enhancement of the dromotropic effect of Ado by compound 20 was mediated by activation of $A_1$AdoRs, prolongation of S—H interval caused by Ado in the presence of compound 20 was shown to be reversed by 10 µM of the $A_1$AdoR antagonist CPX (FIG. 4B). The reversal of the effects of compound 20 by CPX establishes that the enhancement was mediated through the $A_1$AdoR.

EXAMPLES

The following examples illustrate aspects of this invention but should not be construed as limitations. The symbols and conventions used in these examples are intended to be consistent with those used in the contemporary, international, chemical literature, for example, the *Journal of the American Chemical Society* ("*J. Am. Chem. Soc.*") and *Tetrahedron.*

Example 1

Preparation of (2-Amino-4,5-dimethyl-3-thienyl)-(phenyl)methanone: Compound 1

A. General Procedure for the Preparation of Phenacylbromides, the Compounds of Formula (V).

A solution of bromine (55 mmol) in acetic acid (50 mL)is added dropwise to a acetophenone (50 mmol), which is a compound of formula (IV), in glacial acetic (100 ml) in half an hour, with stirring. The resulting suspension is heated at 50° C. for an hour, and then poured into ice water (500 mL). The precipitated phenacyl bromide, a compound of formula (V), is filtered and washed with cold water three times, and finally crystallized from ethanol. (See Rather and Reid, *J. Am. Chem. Soc.* 41, 77 (1919)).

B. General Procedure for the Preparation of Substituted Benzoyl Acetonitriles, the Compounds of Formula (III)

A solution of the phenacyl bromide as prepared in Step A, above, in ethanol is reacted with an aqueous solution of potassium cyanide dissolved in distilled water. The reaction is monitored by TLC control and during this time the solution changes color from yellow-orange to yellow-red. When the reaction is complete, crushed ice is added in a large amount and the solution is acidified with acetic acid. The precipitated corresponding benzoyl acetonitriles are filtered, washed with cold water and then air dried.

C. Preparation of (2-amino-4,5-dimethyl-3-thienyl)-(phenyl)methanone

A mixture of equimolar amounts of methylethyl ketone (0.01 mol), which is a compound of formula (II) wherein $R_5$ and R$_6$ are methyl, benzoyl acetonitrile (0.01 mol), which is a compound of formula (III) wherein R$_2$, R$_3$, and R$_4$ are hydrogen, sulfur (0.01 mol) and morpholine (0.01 mol) in ethanol (4 mL) was stirred and heated at 60° C. for an hour (TLC control). After this time, the suspension was left standing overnight and the mixture was poured into water and the precipitated solid was extracted with ethyl acetate (3×50 mL). The organic layers were dried over magnesium sulfate and evaporated under vacuum. The crude product was chromatographed on silica gel column using mixtures of ethyl acetate and petroleum ether. (m.p. 140–141° C., 80% yield). $^1$H-NMR: (CDCl$_3$):1.53 (s, 3H), 2.13 (s, 3H); 6.44 (sb, 2H); 7.43–7.54 (m, 5H).

Examples 2–6

Compounds 2–6

The following compounds of formula (IB) were prepared using the procedure of Scheme 1 taught herein above, and in an analogous manner to Example 1 using appropriate precursor compounds of formula (II) and formula (III). If the desired compounds of formulas (II) and (III) are not commercially available, they may be prepared according to Example 1, Sections A and B.

2: Preparation of (2-amino-4,5-dimethyl-3-thienyl)-[(3,5-dichloro-4-amino)-phenyl)] methanone (m.p. 155–157° C., 88% yield). $^1$H-NMR: (CDCl$_3$): 1.71 (s, 3H), 2.16 (s, 3H); 4.79 (sb, 2H); 6.03 (sb, 2H); 7.48 (s, 2H).

3: Preparation of (2-amino-4,5-dimethyl-3-thienyl)-(4-chloro-phenyl)methanone (m.p. 128–130° C., 89% yield). $^1$H NMR: (CDCl$_3$): 1.54 (s, 3H), 2.13 (s, 3H); 6.47 (sb, 2H); 7.35–7.48 (m, 4H).

4: Preparation of (2-amino-4,5-dimethyl-3-thienyl)-[3-(trifluoromethyl)-phenyl]methanone (m.p. 103–105° C., 78% yield); $^1$HNMR: (CDCl$_3$): 1.48 (s, 3H), 2.13 (s, 3H); 6.67 (sb, 2H); 7.54–7.75 (m, 4H).

5: Preparation of (2-amino-3-thienyl)-(4-chlorophenyl) methanone (m.p. 178–180° C., 81% yield). $^1$H NMR: (DMSO-d6) 6.27 (d, 1 H), 6.72 (d, 1 H); 7.52–7.63 (m, 4H); 8.39 (sb, 2H).

6: Preparation of (2-amino-3-thienyl)-phenylmethanone (m.p. 150–152° C., 75% yield). $^1$H NMR: (CDCl$_3$): 6.11 (d, 1H), 6.87 (d,1H); 7.05 (sb, 2H); 7.3–7.7 (m, 5H).

Example 7

Preparation of 2-Amino-3-benzoyl-6-benzyloxycarbonyl-4,5,6,7-tetrahydro-thieno[2,3-c] pyridine: Compound 7

A. Preparation of 8-benzyloxycarbonyl 1,4-dioxa-8-azaspiro [4,5] decane

To a well-stirred and ice-cooled solution of 1,4-dioxa-8-azaspiro[4.5]decane (34.9 mmol, 5 g) in dichloromethane (200 mL) under an argon atmosphere, was added triethylamine (52.4 mmol, 7.3 mL) and then benzyloxycarbonyl chloride (42 mmol, 5.93 mL) dropwise. The suspension was stirred at room temperature for 24 hours and the precipitated solid was filtered. The organic solution was evaporated under vacuum to give an oily residue which was chromatographed on silica gel eluting with a mixture of ethyl ether and petroleum ether to afford 8-benzyloxycarbonyl 1,4-dioxa-8-azaspiro [4,5] decane in quantitative yield. $^1$H-NMR (CDCl$_3$): 1.63 (m, 4H); 3.56 (m,4H); 3.89 (s, 4H); 5.09 (s, 2H); 7.28 (s, 5H).

B. Preparation of 1-benzyloxycarbonyl piperidin-4-one

To a stirred solution of 8-benzyloxycarbonyl 1,4-dioxa-8-azaspiro[4,5] decane (0.037 mol, 10 g) in tetrahydrofuran (150 mL) was added a solution of hydrochloric acid 5% (20 mL) dropwise at room temperature. The solution was stirred for 18 h (TLC control) and then evaporated under vacuum to small volume (20 mL) and neutralized with a saturated sodium bicarbonate solution. The aqueous solution was extracted with ethyl acetate (3×100 mL) and the organic layers were dried over sodium sulfate and finally evaporated under vacuum to give 1-benzyloxycarbonyl piperidin-4-one which was substantially pure and which was used in the next step without any purification (92% yield). $^1$H-NMR (CDCl$_3$): 1.63 (m, 4H); 3.56 (m,4H); 5.09 (s, 2H); 7.28 (s, 5H).

C. Preparation of 2-Amino-3-benzoyl-6-benzyloxycarbonyl-4,5,6,7-tetrahydro-thieno[2,3-c] pyridine A mixture of equimolar amounts of 1-benzyloxycarbonyl piperidine (0.01 mol), benzoyl acetonitrile (0.01 mol), sulfur (0.01 mol) and morpholine (0.01 mol) in ethanol (4 mL) was stirred and heated at 60° C. for 1 h (TLC control). After this time, the suspension was left to stand overnight and the mixture was poured into water and the precipitated solid was extracted with ethyl acetate (3×50 mL). The organic layers were dried over magnesium sulfate and evaporated under vacuum. The crude product was chromatographed on a silica gel column using mixtures of ethyl acetate and petroleum ether. (m.p. 138–140° C., 80% yield). $^1$H-NMR(CDCl$_3$): 1.92 (m, 2H), 3.42 (t, 2H); 4.43 (s, 2H); 5.14 (s, 2H); 6.87 (sb, 2H); 7.35–7.46 (m, 5H).

Example 8

Preparation of 2-Amino-3-benzoyl-4,5,6,7-tetrahydrothieno[2,3-c]pyridine: Compound 8

To a cooled and stirred suspension of protected 2-amino-3-benzoyl-6-benzyloxycarbonyl-4,5,6,7-tetrahydrothieno[2,3-c]pyridine (0.01 mol) in acetic acid (2 mL), as prepared in Example 7, was added a solution of HBr (33%) in acetic acid (10 mL). After stirring at room temperature for 4 h (TLC control), n-hexane was added and the resulting suspension was evaporated under vacuum to give a solid which was dissolved in water (10 mL) and neutralized with NaOH (5% solution). The precipitated solid was chromatographed on a silica gel column eluting with ethyl acetate and petroleum ether mixture to give 2-amino-3-benzoyl-4,5,6,7-tetrahydrothieno[2,3-c]pyridine. (m.p.160–162° C., 92% yield). $^1$H-NMR (CDCl$_3$): 1.86 (m, 1 H); 1.95 (m, 2H); 2.79 (t, 2H); 3.79 (s, 2H).

Example 9

Preparation of 2-Amino-3-(4-chloro-benzoyl)-6-benzyloxycarbonyl-4,5,6,7-tetrahydrothieno[2,3-c] pyridine: Compound 9

The procedure of Example 7 was followed except that a corresponding amount of the 4-chloro-derivative of benzoyl acetonitrile was used in place of benzoyl acetonitrile to yield 2-amino-3-(4-chloro-benzoyl)-6-benzyloxycarbonyl-4,5,6, 7-tetrahydrothieno[2,3-c]pyridine. (m.p. 60–62° C., 88% yield). $^1$H-NMR (CDCl$_3$): 1.94 (m, 2H), 3.45 (t, 2H); 4.44 (s, 2H); 5.16 (s, 2H); 6.85 (sb, 2H); 7.36–7.45 (m, 4H).

Example 10

Preparation of 2-Amino-3-(4-chloro-benzoyl) 4,5,6, 7-tetrahydrothieno[2,3-c]pyridine: Compound 10

The procedure of Example 8 was followed except that a corresponding amount of 2-amino-3-(4-chloro-benzoyl)-6- benzyloxycarbonyl-4,5,6,7-tetrahydro-thieno[2,3-c] pyridine, prepared as in Example 9, was used in place of 2-amino-3-benzoyl-6-benzyloxycarbonyl-4,5,6,7-tetrahydrothieno[2,3-c]pyridine. (m.p. 164–166° C., 90% yield). $^1$H-NMR (CDCl$_3$): 1.74 (m, 1 H); 1.89 (m, 2H); 2.84 (t, 2H); 3.82 (s, 2H); 6.85(sb, 2H), 7.29–7.48 (m, 5H).

Example 11

Preparation of 2-Amino-3-[3-(trifluoromethyl)-benzoyl]-6-(3-phenylprop-1-yl)-4,5 6,7-tetrahydrothieno[2,3-c]pyridine: Compound 11

A mixture of equimolar amounts of 3-phenylpropylpiperidin-4-one (0.01 mol) (prepared by a procedure corresponding to that of Example 7, Steps A and B), 3-trifluoromethyl benzoyl acetonitrile (0.01 mol), sulfur (0.01 mol) and morpholine (0.01 mol) in ethanol (4 mL) was stirred and heated at 60° C. for 1 hour (TLC control). After this time, the suspension was allowed to stand overnight and the mixture was poured into water and the precipitated solid was extracted with ethyl acetate (3×50 mL). The organic layers were dried on magnesium sulfate and evaporated under vacuum. The crude product was chromatographed on silica gel column using mixtures of ethyl acetate and petroleum ether. (m.p. 176–178° C.; 78% yield). $^1$H-NMR (CDCl$_3$): 1.88–2.00 (m, 4H); 2.45–2.71(m, 6H); 3.44 (s, 2H); 6.83(sb, 2H); 7.17–7.48 (m, 9H).

Example 12

Preparation of 2-Amino-3-(4-chloro-benzoyl)-6-(phenylmethyl)-4,5,6,7-tetrahydrothieno[2,3-c] pyridine: Compound 12

The same procedure as Example 11 was used except that a corresponding amount of benzylpiperidin-4-one was used in place of 3-phenylpropylpiperidin-4-one and a corresponding amount of 4-chlorobenzoyl acetonitrile was used in place of 3-trifluoromethyl benzoyl acetonitrile. (m.p. 155–157° C.; 78% yield).

Example 13

Preparation of 2-Amino-3-[3-(fluoromethyl)-benzoyl]-6-(phenylmethyl)-4,5,6,7-tetrahydrothieno [2,3-c]pyridine: Compound 13

The same procedure as Example 11 was used except that a corresponding amount of benzylpiperidin-4-one was used in place of 3-phenylpropylpiperidin-4-one. (m.p. 58–60° C.; 88% yield). 1 H-NMR (CHCl$_3$): 1.78–1.87 (m, 2H); 2.48 (t, 2H); 3.42 (s, 2H); 3.63 (s,2H); 7.01 (sb, 2H); 7.28–7.74 (m, 9H).

Example 14

Preparation of 2-Amino-3-(4-chloro-benzoyl)-6-(2-phenyleth-1-yl)-4,5,6,7-tetrahydrothieno[2,3-c] pyridine: Compound 14

The same procedure as Example 11 was used except that a corresponding amount of phenylethylpiperidin-4-one was used in place of 3-phenylpropylpiperidin-4-one and a corresponding amount of 4-chlorobenzoyl acetonitrile was used in place of 3-trifluoromethyl benzoyl acetonitrile. (m.p. 148–150° C.; 62% yield).

Example 15

Preparation of 2-amino-3-[3-(trifluoromethyl)-benzoyl]-6-(2-phenyleth-1-yl)-4,5,6,7-tetrahydrothieno[2,3-c]pyridine: Compound 15

The same procedure as Example 11 was used except that a corresponding amount of benzylpiperidin-4-one was used in place of 3-phenylpropylpiperidin-4-one. (m.p. 137–138° C.; 81% yield). $^1$H-NMR (CHCl$_3$): 1.89 (m, 2H); 2.54 (t, 2H); 2.67–2.87 (m, 4H); 3.51 (s, 2H); 6.99 (sb, 2H); 7.17–7.33 (m, 5H); 7.53–7.74 (m, 4H).

Example 16

Preparation of 2-Amino-3-(4-chloro-benzoyl)-6-(3-phenylprop-1-yl)-4,5,6,7-tetrahydrothieno[2,3-c] pyridine: Compound 16

The same procedure as Example 11 was used except that a corresponding amount of 4-chlorobenzoyl acetonitrile was used in place of 3-trifluoromethyl benzoyl acetonitrile. (m.p. 98–100° C.; 65% yield).

Example 17

Preparation of 2-Amino-3-benzoyl-6-methyl-4,5,6,7-tetrahydrothieno[2,3-c]pyridine: Compound 17

2-Amino-3-benzoyl-4,5,6,7-tetrahydrothieno[2,3-c]pyridine (2 mmol), as prepared in Example 8, and methyl iodide (3 mmol) were dissolved in dry dimethyformamide (20 mL). Finely ground anhydrous potassium carbonate (1.9 g) and sodium iodide (0.2 g) were added to the solution and the resulting mixture was warmed to 65° C. overnight under nitrogen. After this period (TLC control), the reaction mixture was cooled, diluted with water, extracted with diethyl ether (3×50 mL), and dried on sodium sulfate. The crude product was isolated and then purified by column chromatography eluting with ethyl acetate and petroleum ether solutions to give the desired compound. (m.p. 164–165° C.; 77% yield).

Example 18

Preparation of 2-Amino-3-(4-chloro-benzoyl)-6-(ethoxycarbonylmethyl)-4,5,6,7-tetrahydrothieno[2, 3-c]pyridine: Compound 18

The same procedure as Example 17 was used except an equivalent amount of 2-amino-3-(4-chloro-benzoyl) 4,5,6, 7-tetrahydrothieno[2,3-c]pyridine was used in place of 2-Amino-3-benzoyl-4,5,6,7-tetrahydrothieno[2,3-c]pyridine (2 mmol), and an equivalent amount of ethoxycarbonylmethyl iodide was used in place of methyl iodide (3 mmol). (m.p. 105–106° C.; 70% yield).

Example 19

Preparation of 2-Amino-3-benzoyl-6-(ethoxycarbonylmethyl)-4,5,6,7-tetrahydrothieno[2, 3-c]pyridine: Compound 19

The same procedure as Example 17 was used except an equivalent amount of ethoxycarbonylmethyl iodide was used in place of methyl iodide (3 mmol). (m.p. 115–117° C.; 83% yield).

Example 20

Preparation of 2-Amino-3-benzoyl-6-(3-methylbut-2-en-yl)-4,5,6,7-tetrahydrothieno[2,3-c]pyridine: Compound 20

The same procedure as Example 17 was used except an equivalent amount of dimethylallyl iodine was used in place of methyl iodide (3 mmol). (m.p. 76–78° C. 90% yield). $^1$H-NMR (CDCl$_3$): 1.63 (s, 3H); 1.73 (s, 3H); 1.94 (m, 2H);

2.44 (t, 2H); 3.06 (d, 2H); 3.42 (s, 2H); 5.26 (t, 1 H); 6.80 (sb, 2H); 7.35–7.50 (m, 5H).

Example 21

Preparation of 2-Amino-3-(4-chloro-benzoyl)-6-[4-nitro-(2-phenyleth-1-yl)]-4,5,6,7-tetrahydrothieno[2,3-c]pyridine: Compound 21

The same procedure as Example 17 was used except an equivalent amount of 2-amino-3-(4-chloro-benzoyl) 4,5,6,7-tetrahydrothieno[2,3-c]pyridine was used in place of 2-Amino-3-benzoyl-4,5,6,7-tetrahydrothieno[2,3-c]pyridine (2 mmol), and an equivalent amount of p-nitrophenylethyl iodide was used in place of methyl iodide (3 mmol). (m.p. 150–152° C.; 72% yield).

Example 22

Preparation of 2-Amino-3-benzoyl-6-[4-nitro-(2-phenyleth-1-yl)]-4,5,6,7-tetrahydrothieno[2,3-c]pyridine: Compound 22

The same procedure as Example 17 was used except an equivalent amount of p-nitrophenylethyl iodide was used in place of methyl iodide (3 mmol). (m.p. 89–91° C.; 70% yield).

Example 23

Preparation of 2-Amino-3-benzoyl-6-[2-t-butoxycarbonylamino-3-(4-hydroxyphenyl)-propion-1-yl]-4,5,6,7-tetrahydrothieno[2,3-c]pyridine: Compound 23

To an ice-cooled and stirred solution of 2-amino-3-benzoyl-4,5,6,7-tetrahydrothieno[2,3-c]pyridine (0.775 mmol) in dry DMF (11 mL), was added BOC-Tyr-OH (0.08 mmol) and EDCI (0.08, 0.445 g) under argon atmosphere. After stirring overnight, the mixture was evaporated under vacuum to give a solid residue, which was dissolved in saturated sodium bicarbonate solution and was extracted with ethyl acetate (3×20 mL), then dried on magnesium sulfate. The organic layers were evaporated under vacuum to give a solid which was chromatographed on silica gel column eluting with ethyl acetate and petroleum ether solution to afford 2-amino-3-benzoyl-6-[2-t-butoxycarbonylamino-3-(4-hydroxyphenyl)-propion-1-yl]-4,5,6,7-tetrahydrothieno[2,3-c]pyridine as a yellow solid. (m.p. 143–145° C., 84% yield).

Example 24

Preparation of 2-Amino-3-benzoyl-4,5,6,7-tetrahydrobenzo[b]thiophene: Compound 24

The same procedure as Example 1 was used except a corresponding amount of cyclohexanone was used in place of methylethyl ketone. (m.p.150–152° C., 75% yield). $^1$H-NMR (CDCl$_3$): 1.46–1.49 (m,2H), 1.69–1.80 (m,4H); 2.47–2.54 (m, 2H); 6.71 (sb, 2H); 7.37–7.50 (m, 5H).

Example 25

Preparation of 4-Phenyl-5,6,7,8-tetrahydro[1]Benzothieno[2,3-d]pyrimidine: Compound 25

A suspension of 2-amino-3-thienyl)-phenylmethanone (5 mmol) in formamide (7 mL) was heated at 180° C. for 5 hours in an open vessel. The residue was diluted with dimethylformamide (5 mL), treated with charcoal, and filtered over a small pad of Celite 503 (brand of filter aid). The cyclized compound was precipitated by addition of water (30 mL) to the filtrate and recrystallized from the same solvents. (m.p. 135–137° C.).

Example 26

Preparation of 2-Methyl,3-ethoxycarbonyl-4-phenyl-5,6,7,8-tetrahydro[1]Benzothieno[2,3-b]pyridine: Compound 26

To an ice-cooled and stirred solution of 2-amino-3-thienyl)-phenylmethanone in absolute ethanol (20 mL), ethyl acetoacetate (0.055 mol) was added. To the mixture sodium ethylate (100 mg) was added at 0° C. and the solution was refluxed for about 10 hours. After completion of the reaction (TLC control), the solution was evaporated under vacuum and the residue was taken up with water (50 mL) and the aqueous solution was extracted with ethyl acetate (3×100 mL). The combined organic layers were dried and evaporated under vacuum to give a yellow residue which was crystallized from tetrahyrofuran/hexane. (m.p. 118–120° C.).

Example 27

Preparation of 2-Amino-3-(4-bromobenzoyl)-cyclopenta[b]thiophene: Compound 27

The same procedure as Example 1 was used except a corresponding amount of cyclopentanone was used in place of methylethyl ketone and an equivalent amount of 4-bromo-benzoyl acetonitrile was used in place of benzoyl acetonitrile. (m.p. 205–206° C., 87% yield). (CDCl$_3$): 2.1–2.13 (m, 4H), 2.63–2.68 (m, 2H); 6.99 (sb, 2H); 7.34 (d,2H);7.53 (d, 2H).

Example 28

Preparation of 2-Amino-3-benzoyl-6-(4-methylphenylsulphonyl)-4,5,6,7-tetrahydrothieno[2,3-c]pyridine: Compound 28

To a well-stirred and ice-cooled solution of 2-amino-3-benzoyl-4,5,6,7-tetrahydrothieno[2,3-c]pyridine (0.78 mmol, 0.2 g) in dichloromethane (20 ml) under an argon atmosphere, was added triethylamine (0.162 ml) and then p-toluenesulfonyl chloride (0.93 mmol, 177 mg) portionwise. The suspension was stirred at room temperature for 24 h and the precipitated solid was filtered. The organic solution was evaporated under vacuum to give a solid residue which was chromatographed on silica gel eluting with ethyl ether and petroleum ether mixture to afford 2-amino-3-benzoyl-6-(4-methylphenylsulphonyl)-4,5,6,7-tetrahydrothieno[2,3-c]pyridine. (m.p.165–167° C., 85 yield). 1 H-NMR (CDCl$_3$): 1.95 (m, 2H); 2.43 (s, 3H); 3.07 (t, 2H); 3.51 (s, 2H); 6.76 (sb, 2H); 7.3–7.67 (m, 9H).

Example 29

Preparation of 4-Phenyl-thieno[2,3-d]pyrimidine: Compound 29

The same procedure as Example 25 was used except a corresponding amount of 2-amino-3-benzoyl-cyclopenta[b]thiophene was used in place of 2-amino-3-thienyl)-phenylmethanone (5 mmol). In turn, 2-amino-3-benzoyl-cyclopenta[b]thiophene can be prepared by the procedure of Example 1.

Example 30

Preparation of 2-amino-3-(4-chlorobenzoyl)-6-(((phenyl)amino)carbonyl)-4,5,6,7-tetrahydrothieno(2,3-c)pyridine: Compound 30

To a stirred solution of 2-amino-3-(4-chlorobenzoyl)-4,5,6,7-tetrahydrothieno(2,3-c)pyridine) (1.02 mmol) in dry $CH_2Cl_2$ (20 mL), $Et_3N$ (1.2 eq) and phenylisocyanate (1.2 eq) were added. The mixture was stirred at room temperature for 4 hours, then was concentrated at reduced pressure and the residue purified by flash chromatography (EtOAc/light petroleum 3/7) to afford the desired compound as a solid (mp 216–217 °C.).

Example 31

Preparation of 2-amino-3-(4-chlorobenzoyl)-6-(3-methyl-but-2-en-1-yl)-4,5,6,7-tetrahydrothieno(2,3-c)pyridine: Compound 31

To a stirred solution of 2-amino-3-(4-chlorobenzoyl-4,5,6,7-tetrahydrothieno(2,3-c)pyridine (0.7 mmol) in dry $CH_2Cl_2$ (20 mL), $Et_3N$ (1.2 equiv.) and 3-methyl-but-2-en-yl bromide were added. The solution was stirred at room temperature for 4 hours, then concentrated and the residue purified by crystallization to afford the title compound as a solid (mp 118–120° C $^1$H NMR (CDCl$_3$) 1.63 (s, 3H); 1.73 (s, 3H); 1.94 (m, 2H); 2.45 (m, 2H); 3.06 (d, 2H, J=7); 3.41 (s, 2H); 5.26 (m, 1H); 6.77 (bs, 2H); 7.39 (d, 2H, J=6.4); 7.42 (d, 2H, J=6.4)

Example 32

Preparation of 2-amino-3-(4-chlorobenzoyl)-6-(prop-2-en-1-yl)-4,5,6,7-tetrahydrothieno(2,3-c)pyridine: Compound 32

To a stirred solution of 2-amino-3-(4-chlorobenzoyl-4,5,6,7-tetrahydrothieno(2,3-c)pyridine (0.7 mmol) in dry $CH_2Cl_2$ (20 mL), $Et_3N$ (1.2 equiv.) and prop-2-en-yl bromide (1.2 eq.) were added. The solution was stirred at room temperature for 4 hours, then concentrated and the residue purified by crystallization to afford the title compound as a solid (mp 118–120° C.). $^1$H NMR (CDCl$_3$) 1.96 (m, 2H); 2.47 (m, 2H); 3.12 (d, 2H, J=6); 3.42 (s, 2.H); 5.14–5.24 (m, 2H); 5.82–5.95 (m, 1H); 6.82 (bs, 2H); 7.35 (d, 2H, J=8); 7.43 (d, 2H, J=8)

Example 33

Preparation of 2-amino-3-(4-iodobenzoyl)-6-(((phenyl)amino)carbonyl)-4,5,6,7-tetrahydrothieno(2,3-c)pyridine: Compound 33

To a stirred solution of 2-amino-3-(4-iodobenzoyl)-4,5,6,7-tetrahydrothieno(2,3-c)pyridine) (1.02 mmol) in dry $CH_2Cl_2$ (20 mL), $Et_3N$ (1.2 eq) and phenylisocyanate (1.2 eq) were added. The mixture was stirred at room temperature for 4 hours, then was concentrated at reduced pressure and the residue purified by flash chromatography (EtOAc/light petroleum 3/7) to afford the desired compound as a solid (mp 89–90 °C.).

Example 34

Preparation of 2-amino-3-(4-bromobenzoyl)-6-(((phenyl)amino)carbonyl)-4,5,6,7-tetrahydrothieno(2,3-c)pyridine: Compound 34

To a stirred solution of 2-amino-3-(4-bromobenzoyl)-4,5,6,7-tetrahydrothieno(2,3-c)pyridine) (1.02 mmol) in dry $CH_2Cl_2$ (20 mL), $Et_3N$ (1.2 eq) and phenylisocyanate (1.2 eq) were added. The mixture was stirred at room temperature for 4 hours, then was concentrated at reduced pressure and the residue purified by flash chromatography (EtOAc/light petroleum 3/7) to afford the desired compound as a solid (mp 89–90 °C.).

Example 35

Preparation of 2-amino-3-(4-bromobenzoyl)-4,5,6,7-tetrahydrothieno(2,3-c)pyridine: Compound 35

Using, the procedures in Examples 7 and 8, substituting p-bromobenzoyl acetonitrile for benzoyl acetonitrile, the title compound was prepared as a solid (mp 185–187° C.).

Example 36

Preparation of 2-amino-3-(4-bromobenzoyl)-6-(3-methyl-but-2-en-1-yl)-4,5,6,7-tetrahydrothieno(2,3-c)pyridine: Compound 36

To a stirred solution of 2-amino-3-(4-bromobenzoyl-4,5,6,7-tetrahydrothieno(2,3-c)pyridine (0.7 mmol) in dry $CH_2Cl_2$ (20 mL), $Et_3N$ (1.2 equiv.) and 3-methyl-but-2-en-yl bromide (1.2 eq.) were added. The solution was stirred at room temperature for 4 hours, then concentrated and the residue purified by crystallization to afford the title compound as a solid (mp 73–75° C. $^1$H NMR (CDCl$_3$) 1.64 (s, 3H); 1.74 (s, 3H); 1.95 (m, 2H); 2.47 (m, 2H); 5.07 (d, 2H, J=7); 3.41 (s, 2H); 5.27 (m, 1H); 6.91 (bs, 2H); 7.34 (d, 2H, J=8.4); 7.52 (d, 2H, J=8.4)

Example 37

Preparation of 2-amino-3-(4-bromobenzoyl)-6-(prop-2-en-1-yl)-4,5,6,7-tetrahydrothieno(2,3-c)pyridine: Compound 37

To a stirred solution of 2-amino-3-(4-bromobenzoyl-4,5,6,7-tetrahydrothieno(2,3-c)pyridine (0.7 mmol) in dry $CH_2Cl_2$ (20 mL), $Et_3N$ (1.2 equiv.) and prop-2-en-yl bromide (1.2 eq.) were added. The solution was stirred at room temperature for 4 hours, then concentrated and the residue purified by crystallization to afford the title compound as a solid (mp 116–118° C. $^1$H NMR (CDCl$_3$) 1.96 (m, 2H); 2.47 (m, 2H); 3.12 (d, 2H, J=6.6); 3.42 (s, 2H); 5.15–5.25 (m, 2H); 5.80–6.00 (m, 1H); 6.81 (bs, 2H); 7.36 (d, 2H, J=8.2); 7.53 (d, 2H, J=8.2)

Example 38

Preparation of 2-amino-3-(4-iodobenzoyl)-4,5,6,7-tetrahydrothieno(2,3-c)pyridine: Compound 38

Using the procedures in Examples 7 and 8, substituting p-iodobenzoyl acetonitrile for benzoyl acetonitrile, the title compound was prepared as a solid mp 230–231° C.

Example 39

Preparation of 2-amino-3-(4-iodobenzoyl)-6-(3-methyl-but-2-en-1-yl)-4,5,6,7-tetrahydrothieno(2,3-c)pyridine: Compound 39

To a stirred solution of 2-amino-3-(4-iodobenzoyl-4,5,6,7-tetrahydrothieno(2,3-c)pyridine (0.7 mmol) in dry $CH_2Cl_2$ (20 mL), $Et_3N$ (1.2 equiv.) and 3-methyl-but-2-en-yl bromide (1.2 eq.) were added. The solution was stirred at room temperature for 4 hours, then concentrated and the residue

Example 40

Preparation of 2-amino-3-(4-phenylbenzoyl)-6-(benzyloxycarbonyl)-4,5,6,7-tetrahydrothieno(2,3-c)pyridine: Compound 40

2-Amino-3-(4-phenylbenzoyl)-4,5,6,7-tetrahydrothieno(2,3-c)pyridine was reacted with benzyloxycarbonyl chloride and triethylamine to afford the title compound as a solid (mp 83–85° C.). $^1$H NMR (CDCl$_3$) 2.05 (m, 2H); 3.45 (m, 2H); 4.46 (s, 2H); 5.15 (s, 2H); 6.72 (bs, 2H) 7.35–7.66 (m, 14H)

Example 41

Preparation of 2-amino-3-(4-phenylbenzoyl)-6,6-bis(3-methyl-but-2-en-1-yl)-4,5 6,7-tetrahydrothieno(2,3-c)pyridinium chloride: Compound 41

To a stirred solution of 2-amino-3-(4-phenylbenzoyl-4,5,6,7-tetrahydrothieno(2,3-c)pyridine (0.7 mmol) in dry CH$_2$Cl$_2$ (20 mL), Et$_3$N (1.2 equiv.) and prop-2-en-yl bromide (2.4 eq.) were added. The solution was stirred at room temperature for 4 hours, then concentrated and the residue purified by crystallization to afford the title compound as a solid (mp 183–185° C.). $^1$H NMR (CDCl$_3$) 1.82 (s, 6H); 1.85 (s, 6H); 2.30 (m, 2H); 3.70 (m, 2H); 4.07 (m, 4H); 4.75 (s, 2H); 5.26 (m, 2H); 7.40–8.50 (m, 11H).

Example 42

Preparation of 2-amino-3-(4-fluorobenzoyl)-6-(benzyloxycarbonyl)-4,5,6,7-tetrahydrothieno(2,3-c)pyridine: Compound 42

Using the procedures in Examples 7 and 8, substituting p-fluorobenzoyl acetonitrile for benzoyl acetonitrile, 2-amino-3-(4-fluorobenzoyl)-4,5,6,7-tetrahydrothieno(2,3-c)pyridine was prepared. This compound was reacted with benzyloxycarbonyl chloride to yield the title compound as a solid (mp 90–92° C). $^1$H NMR (CDCl$_3$) 1.96 (m, 2H); 3.45 (m, 2H); 4.45 (s, 2H); 5.15 (s, 2H); 6.71 (bs, 2H); 7.05–7.52 (m, 9H).

Example 43

Preparation of 2-amino-3-(4-phenylbenzoyl)-4,5,6,7-tetrahydrothieno(2,3-c)pyridine: Compound 43

Using the procedures in Examples 7 and 8, substituting p-phenylbenzoyl acetonitrile for benzoyl acetonitrile, the title compound was prepared as a solid (mp 185–187° C.). $^1$H NMR (CDCl$_3$) 1.75 (m, 2H); 2.40 (bs, 1H); 2.6 (m, 2H); 3.59 (s, 2H); 7.44–7.776 (m, 9H); 8.16 (bs, 2H).

Example 44

Preparation of 2-amino-3-(4-phenylbenzoyl)-6.6-bis(prop-2-en-1-yl)-4,5,6,7-tetrahydrothieno(2,3-c)pyridinium chloride: Compound 44

To a stirred solution of 2-amino-3-(4-phenylbenzoyl-4,5,6,7-tetrahydrothieno(2,3-c)pyridine (0.7 mmol) in dry CH$_2$Cl$_2$ (20 mL), Et$_3$N (1.2 equiv.) and prop-2-en-yl bromide (2.4 eq.) were added. The solution was stirred at room temperature for 4 hours, then concentrated and the residue purified by crystallization to afford the title compound as a solid (mp 149–151° C.).

Example 45

Preparation of 2-amino-3-cyano-4-phenyl-5,6,7,8-tetrahydro(1)benzothieno(2,3-b)pyridine: Compound 45

The title compound was prepared by reacting 2-amino-3-benzoyl-4,5,6,7-tetrahydrothieno[2,3-c]pyridine, as prepared in Example 8, with the carbanion of malonodinitrile to yield a solid (mp 152–154° C.).

Example 46

Preparation of 2-hydroxy-3-cyano-4-phenyl-5,6,7,8-tetrahydro(1)benzothieno(2,3-b)pyridine: Compound 46

The title compound was prepared by reacting 2-amino-3-benzoyl-4,5,6,7-tetrahydrothieno[2,3-c]pyridine, as prepared in Example 8, with the carbanion of ethylcyanoacetate to yield a solid (mp 206° C.).

Example 47

Pharmaceutical Formulations

| (A) Transdermal System - for 1000 patches | |
|---|---|
| Ingredients | Amount |
| Active compound | 100 g |
| Silicone fluid | 450 g |
| Colloidal silicon dioxide | 2 g |

The silicone fluid and active compound are mixed together and the colloidal silicone dioxide is added to increase viscosity. The material is then dosed into a subsequent heat sealed polymeric laminate including the following: polyester release liner, skin contact adhesive composed of silicone or acrylic polymers, a control membrane which is a polyolefin, and an impermeable backing membrane made of a polyester multilaminate. The resulting laminated sheet is then cut into 10 sq. cm patches

| (B) Oral Tablet - For 1000 Tablets | |
|---|---|
| Ingredients | Amount |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

| (C) Injection - for 1000, 1 mL Ampules | |
|---|---|
| Ingredients | Amount |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

| (D) Continuous Injection - for 1000 mL | |
|---|---|
| Ingredients | Amount |
| Active compound | 10 g |
| Buffering agents | q.s. |
| Water for injection | q.s. 1000 mL |

Example 48

Evaluation of Compounds

The compounds described in Examples 1–29 above were assayed for their allosteric enhancing ability at the adenosine A, receptor. These are listed as T1 through T29 below.

Materials and Methods

Compounds T1 through T29 were provided by Medco Research, Inc. The adenosine $A_1$ receptor agonist $N^6$ cyclopentyladenosine (CPA) and the adenylyl cyclase activator forskolin were purchased from Research Biochemicals, Inc. Rolipram was a gift from Berlex Labs. Adenosine deaminase was purchased from Sigma Chemical. Ham's F-12 culture medium and fetal bovine serum were purchased from GIBCO Life Technologies. Cell culture plasticware and antibiotic G-418 were from Fisher Scientific.

The preparation chosen for the assay of the compounds was the Chinese hamster ovary (CHO) cell expressing human recombinant adenosine $A_1$ receptors at a density of around 8000 fmol/mg protein. These cells were cultured using known techniques (Shryock et al., *Mol. Pharmacol.*, 1998, 53:886–893, the contents of which are hereby incorporated by reference).

Protocol

The effect of each compounds on cAMP content of cultured CHO cells was determined in the presence of forskolin (1–1.5 μM), rolipram (20 μM), the adenosine receptor agonist CPA (0.05–0.1 μM) and adenosine deaminase (2 U/mL). Forskoline was used to increase the activity of adenylyl cyclase and the content of cAMP in cells, and rolipram was used to inhibit the activity of cAMP phosphodiesterases that degrade cAMP. Adenosine deaminase was used to degrade endogenous adenosinein the incubation medium.

To begin an experiment, CHO cells grown in individual wells of 12-well culture plates were washed once with Hank's buffered saline solution to remove growth medium. The Hank's solution was itself then removed and replaced with fresh Hank's solution at 36° C. containing forskolin, rolipram, CPA, adenosine deaminase, and the compound to be assayed. After an incubation of six minute duration, this solution was removed and replaced with 50 mM hydrochloric acid to terminate the effect of the drug, lyse the cells, and prevent further enzymatic formation and metabolism of cAMP. The cAM content of acid extracts of cells was determined by radioimmunoassay as previously described (Shryock et al., *Mol. Pharmacol.*, 1998, 53:886–893). In each experiment, 4–5 compounds were tested in parallel, at each of four concentrations, 0.01, 0.1, 1 and 10 μM. As a control, the effect of CPA (0.1–10 nM) was determined in each experiment. Protein content of cell samples was measured by the method of Bradford using a kit form Bio-Rad with albumin as a reference standard.

Results

The compounds acted to both enhance and antagonize the effect of the adenosine $A_1$ receptor agonist, CPA, on CHO cells expressing adenosine $A_1$ receptors. The effects of all twenty nine compounds are shown in FIGS. 5–10 (bar graphs) and FIGS. 11–16 (concentration response plots). Compounds T3, T5, T7, T9, T13, T19 and T21 decreased cAMP content in the presence of a low concentration of CPA (0.05–0.1 nM). These compounds are thus indicated by the CHO cell assay to be allosteric enhancers of the action of an adenosine $A_1$ receptor agonist. Compounds T5, T7, T9, and T13 appear to be the best enhancers. Compound T7 had the highest potency and efficacy (maximal effect).

Several compounds (i.e., T11, T12, T23, T24, and T27) acted as antagonists of the action of CPA. Two compounds (T6 and T15) at a low concentration enhanced the action of CPA, but at a higher concentration antagonized the action of CPA.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for providing cardioprotection, neuroprotection, pain management, reduction of free fatty acids, triglycerides, or glucose levels, adjunct therapy in diabetes, treatment of GI disorders, treatment of glaucoma; treatment of sleep disorders; treatment of cardiac disarrythmias (peroxysmal supraventricular tachycardia), treatment of congestive heart failure or treatment of inflammation comprising administering to a patient in need of treatment thereof an effective amount to treat the disorder of a compound selected from a group consisting of compounds of formulas:

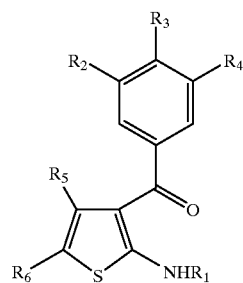

wherein:

R₁ is hydrogen, alkyl, substituted alkyl, or haloacetyl;

R₂, R₃, and R₄ are independently hydrogen, halogen, alkyl, substituted alkyl, aryl, heteroaryl, heterocyclic, lower alkenyl, lower alkanoyl, amino, trifluoromethyl, amino alkyl, nitro, or cyano.

2. The method of claim 1, wherein the cardioprotection involves short term protection during surgical procedures selected from the group consisting of percutaneous angioplasty (PTDA), angioplasty, and cardiac surgeries.

3. The method of claim 1, wherein the cardioprotection involves long term protection from myocardial infarction.

4. The method of claim 1, wherein the neuroprotection involves stroke prevention, stroke treatment, or the treatment of epilepsy.

5. The method of claim 1, wherein the pain management involves the treatment of diabetic neuropathy, post herpetic neuralgia or other forms of neuropathic pain.

6. The method of claim 5 wherein the treatment involves acute i.v. injection, chronic oral administration or chronic intraveneous injection.

7. The method of claim 1, wherein the treatment of diabetes includes the treatment of insulin and non-insulin dependent diabetes mellitus, the stimulation of insulin secretion from the pancreas, or the increase in tissue sensitivity to insulin.

8. The method of claim 1, wherein the treatment of GI disorders involves treating a disorder selected from the group consisting of diarrhea, irritable bowel disease, irritable bowel syndrome, and incontinence.

9. The method of claim 1 wherein:

R₁ is hydrogen,

R₂, R₃, and R₄ are independently hydrogen, halogen, or trifluoromethyl.

* * * * *